(12) United States Patent
La Lumondiere et al.

(10) Patent No.: US 8,450,688 B2
(45) Date of Patent: May 28, 2013

(54) REFRACTION ASSISTED ILLUMINATION FOR IMAGING

(75) Inventors: Stephen La Lumondiere, Torrance, CA (US); Terence Yeoh, Pasadena, CA (US); Martin Siu Wo Leung, Redondo Beach, CA (US); Neil A. Ives, Hawthorne, CA (US); William T. Lotshaw, Rancho Palos Verdes, CA (US); Steven C. Moss, Hermosa Beach, CA (US)

(73) Assignee: The Aerospace Corporation, El Segundo, CA (US)

( * ) Notice: Subject to any disclaimer, the term of this patent is extended or adjusted under 35 U.S.C. 154(b) by 0 days.

(21) Appl. No.: 13/190,264

(22) Filed: Jul. 25, 2011

(65) Prior Publication Data
US 2012/0019707 A1    Jan. 26, 2012

Related U.S. Application Data

(63) Continuation-in-part of application No. 12/661,967, filed on Mar. 26, 2010, which is a continuation-in-part of application No. 12/590,262, filed on Nov. 5, 2009, now Pat. No. 8,138,476.

(51) Int. Cl.
*G01J 5/02* (2006.01)

(52) U.S. Cl.
USPC .................................................. 250/339.11

(58) Field of Classification Search
USPC   250/339.01–339.15, 572, 563, 562; 356/239, 356/430, 431, 240
See application file for complete search history.

(56) References Cited

U.S. PATENT DOCUMENTS

| 5,131,963 A | 7/1992 | Ravi |
| 5,192,980 A | 3/1993 | Dixon et al. |

(Continued)

FOREIGN PATENT DOCUMENTS

| EP | 0887621 A1 | 12/1998 |
| WO | WO 98/21687 | 5/1998 |

(Continued)

OTHER PUBLICATIONS

G. Springholz, "Strain contrast in scanning tunneling microscopy imaging of subsurface feature dislocations in lattice-mismatched heteroepitaxy," 1997, Applied Surface Science, vol. 112, pp. 12-22.*

(Continued)

*Primary Examiner* — Kiho Kim
(74) *Attorney, Agent, or Firm* — K & L Gates LLP

(57) ABSTRACT

Various embodiments are directed to systems and methods for imaging subsurface features of a semiconductor object comprising a first region having a first doping property and a second region having a second doping property. The semiconductor object may comprise subsurface features and material between a surface of the semiconductor object and the subsurface features. The material may have an index of refraction that is greater than an index of refraction of a surrounding medium in contact with the surface of the semiconductor object. For example, a system may comprise an imaging device comprising an objective. The imaging device may be sensitive to a first wavelength. The system may also comprise an illumination source to emit illumination substantially at the first wavelength. The illumination may be directed towards the surface of the semiconductor object at a first angle relative to a normal of the surface. The first angle is greater than an acceptance angle of the objective of the imaging device. Also, the first wavelength may have a photonic energy substantially equal to a bandgap of the first region.

30 Claims, 18 Drawing Sheets

U.S. PATENT DOCUMENTS

| | | | |
|---|---|---|---|
| 5,196,716 | A | 3/1993 | Moriya et al. |
| 5,220,403 | A | 6/1993 | Batchelder et al. |
| 5,754,514 | A | 5/1998 | Guerra |
| 5,757,050 | A | 5/1998 | Adler et al. |
| 5,900,354 | A | 5/1999 | Batchelder et al. |
| 5,930,588 | A | 7/1999 | Paniccia |
| 5,946,543 | A | 8/1999 | Kimura et al. |
| 5,966,019 | A * | 10/1999 | Borden ............... 324/754.22 |
| 6,005,965 | A | 12/1999 | Tsuda et al. |
| 6,055,055 | A | 4/2000 | Toh |
| 6,266,130 | B1 | 7/2001 | Hasegawa et al. |
| 6,734,960 | B1 | 5/2004 | Goto et al. |
| 6,859,516 | B2 | 2/2005 | Schneider et al. |
| 6,906,801 | B2 | 6/2005 | Borden et al. |
| 7,890,158 | B2 * | 2/2011 | Rowe et al. ............... 600/476 |
| 8,212,215 | B2 | 7/2012 | La Lumondiere et al. |
| 8,254,020 | B2 * | 8/2012 | Holy et al. ............... 359/385 |
| 2002/0005493 | A1 * | 1/2002 | Reese et al. ............... 250/459.1 |
| 2002/0176454 | A1 * | 11/2002 | Arbore et al. ............... 372/20 |
| 2002/0180965 | A1 | 12/2002 | Engelhardt et al. |
| 2004/0119018 | A1 | 6/2004 | Alfano et al. |
| 2005/0001900 | A1 | 1/2005 | Kreh et al. |
| 2005/0231713 | A1 | 10/2005 | Owen et al. |
| 2005/0245005 | A1 | 11/2005 | Benson |
| 2007/0031995 | A1 | 2/2007 | Kaneko |
| 2008/0240548 | A1 | 10/2008 | Yeoh et al. |
| 2009/0002688 | A1 | 1/2009 | Soeda et al. |
| 2009/0045415 | A1 | 2/2009 | Koshiba |
| 2009/0066933 | A1 | 3/2009 | Takano et al. |
| 2011/0102615 | A1 | 5/2011 | La Lumondiere et al. |
| 2011/0102770 | A1 | 5/2011 | La Lumondiere et al. |

FOREIGN PATENT DOCUMENTS

| | | |
|---|---|---|
| WO | WO 2008/119550 A1 | 10/2008 |
| WO | WO 2008/120883 A1 | 10/2008 |

OTHER PUBLICATIONS

Ramsay et al., "Three-dimensional nanometric sub-surface imaging of a silicon flip-chip using the two-photon optical beam induced current method," 2007, Microelectronics Reliability, vol. 47, pp. 1534-1538.*

Pfister et al., "Surface and subsurface imaging of indium in InGaAs by scanning tunneling microscopy," 1996, Applied Surface Science, vol. 104/105, pp. 516-521.*

Office Action mailed Jul. 27, 2011 in U.S. Appl. No. 12/590,262.

Notice of Allowance mailed Nov. 14, 2011 in U.S. Appl. No. 12/590,262.

Vasefi et al., "An Optical Imaging Technique Using Deep Illumination in the Angular Domain," 2007, IEEE Journal of Selected Topics in Quantum Electronics, vol. 13, No. 6, pp. 1610-1620.

Office Action mailed Nov. 26, 2010 in U.S. Appl. No. 12/590,262.

Office Action mailed Mar. 24, 2011 in U.S. Appl. No. 12/590,262.

International Search Report and Written Opinion of the International Search Authority mailed in Application No. PCT/US2010/046978 on Dec. 17, 2010.

International Search Report and Written Opinion of the International Search Authority mailed in Application No. PCT/US2011/028514 on Jun. 24, 2011.

Non-Final Office Action mailed Aug. 1, 2012 in U.S. Appl. No. 12/661,967.

Notice of Allowance mailed Nov. 14, 2012 in U.S. Appl. No. 12/661,967.

Notice of Allowance mailed Mar. 20, 2012 in U.S. Appl. No. 13/368,026.

* cited by examiner

REFRACTION ASSISTED ILLUMINATION FOR IMAGING

PRIORITY CLAIM

This application is a continuation-in-part of co-pending U.S. application Ser. No. 12/661,967 filed on Mar. 26, 2010, which is incorporated herein by reference in its entirety and is also a continuation-in-part of co-pending U.S. application Ser. No. 12/590,262 filed on Nov. 5, 2009, which is also incorporated herein by reference in its entirety.

BACKGROUND

In semiconductor fabrication and other fields, it is often necessary or desirable to image subsurface objects. For example, when a semiconductor chip is constructed according to "flip-chip" mounting techniques, component structures on the chip are obscured by the substrate. Various semiconductor fabrication and testing techniques require high-contrast imaging of components. Some examples of these techniques include Laser Assisted Chemical Etching, Focused Ion Beam, and others. Imaging through common substrate materials, such as silicon, is possible, although, difficulties exist.

One method of imaging through substrate material is conventional bright field microscopy. According to bright field microscopy, illumination is provided in a direction normal to the substrate surface. An image is captured with a camera or other imaging device also oriented normal to the substrate surface. While this technique can be relatively inexpensive, the resolution of the resulting images is often disappointing. This is, at least in part, because backscatter off of the substrate is directed back towards, and captured by, the objective lens of the imaging device. This has the effect of blurring and washing out the resulting image. It is known to enhance the resolution of bright field microscopy by applying an anti-reflective coating to the substrate. This method, however, is expensive and requires that the target semiconductor chip be subjected to one or more additional processing steps. It is also known to use laser scanning confocal microscopy to achieve higher resolution images through semiconductor substrates. Although laser scanning confocal microscopy does produce good results, the equipment for implementing it is extremely expensive, limiting its practical usefulness.

SUMMARY

In one general aspect, embodiments of the present invention are directed to systems and methods of imaging subsurface features of objects such as, for example, semiconductor devices. An illumination source may be directed towards a surface of an object comprising subsurface features, wherein the illumination from the source is directed at a first angle relative to the normal of the surface. The object may have a portion between the subsurface features and the surface, the portion having an index of refraction that is greater than the index of refraction of a surrounding medium that surrounds the object. An imaging device may be placed with an objective lens oriented substantially normal to the surface. The first angle may be larger than an acceptance angle of the objective lens. In some embodiments, multiple illumination beams may be generated by one or more illumination sources. The beams may be rotated relative to one another about the normal of the surface. Also, in some embodiments, multiple images may be taken with the objective of the imaging device at different positions rotated off of the normal. The multiple images may be combined to generate a composite image. Additionally, in some embodiments, illumination from the illumination source may be filtered and/or tuned to include illumination at a wavelength having a photon energy offset from the bandgap of the object (e.g., when the object is a semiconductor substrate). In various embodiments, the selected wavelength may have a photon energy substantially equal to a bandgap of a doped region of the object. In this way, the illumination may be transmitted by the object, but attenuated by the doped region. The attenuation may be reflected in images of the object, indicating the location of the doped region. Also, in various embodiments, some or all of the imaging embodiments described herein may be implemented utilizing polarization techniques to reduce glare. For example, a polarizer may be placed over at least one of the illumination source or the imaging device. The polarizer may have a polarization direction parallel to the direction of the illumination beam. In this way, specular scatter reaching the imaging device may be minimized.

FIGURES

Various embodiments of the present invention are described here by way of example in conjunction with the following figures, wherein:

FIG. 7 illustrates one embodiment of the object of FIG. 1 showing two subsurface features and the ray reflections there from.

DESCRIPTION

Figure 1:
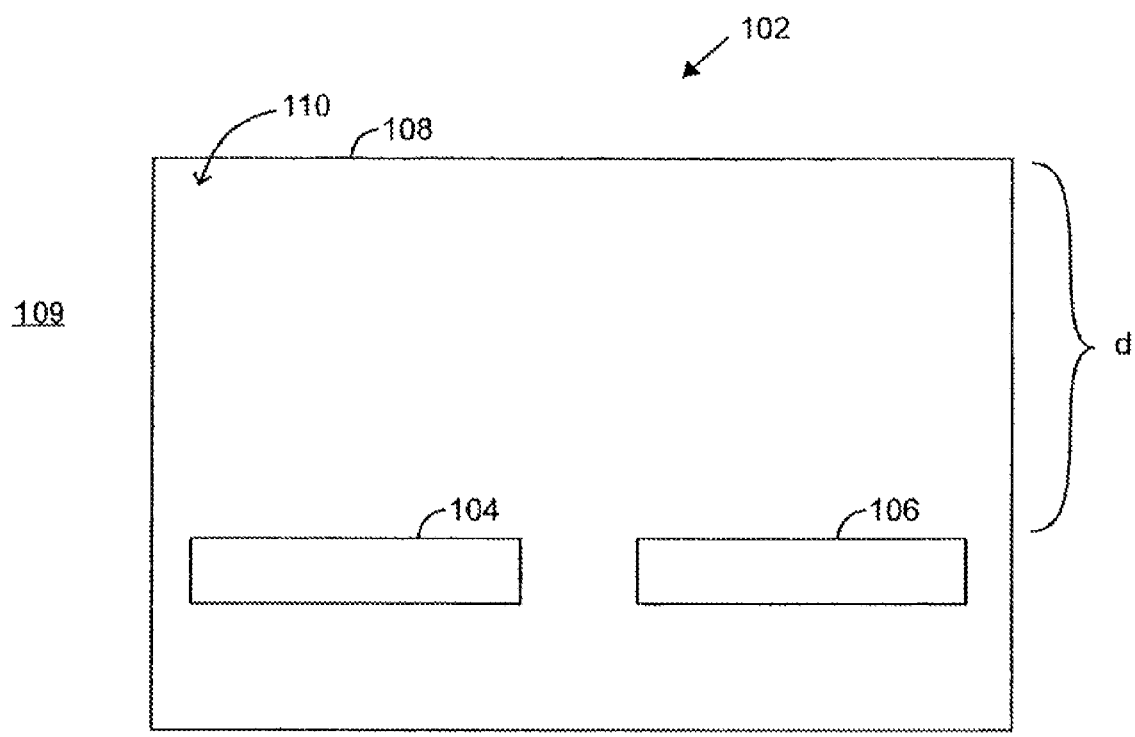
FIG. 1 illustrates a cross-sectional view of one embodiment of an object having subsurface features that may be imaged utilizing the side-addressed illumination techniques described herein.

Various embodiments are directed to systems and methods for imaging subsurface features including, for example, semiconductor components viewed through the backside of a substrate (e.g., "backside imaging"). An illumination source may be side-addressed, or oriented at an angle relative to the normal of the surface to be imaged. An imaging device comprising an objective lens or objective may be positioned with a field of view directed substantially normal to the surface. The side-addressed position of the illumination source may provide increased image resolution in at least two ways. First, specular reflection or back-scatter off of the surface may be directed substantially outside of the acceptance angle of the objective lens. Second, when the surface over the features to be imaged has a relatively high index of refraction, refraction at the interface between the surface and the surrounding medium (e.g., air) may create a spatial filtering effect that further enhances the captured image.

According to various embodiments, it may be desirable to modify the direction of illumination and/or the perspective of the objective. This may result in images with better contrast, which may allow images to better capture feature details. In some embodiments, the surface of the object may be illuminated from multiple directions. For example, multiple side-addressed illumination beams may be directed to an image location on the surface. The illumination beams may be rotated about a normal of the surface. The separation between each of the respective illumination beams may be expressed as an angle about the surface normal. The illumination beams may be provided by a single illumination source that is rotated about the surface normal, or by multiple illumination sources placed at different positions. Also, the illumination beams may be provided simultaneously, serially, or some combination thereof. When the illumination beams are not provided simultaneously, a separate image may be captured for each illumination beam or combination of illumination beams activated at a given time. The resulting images may be combined according to any suitable algorithm to form a composite image. Utilizing multiple illumination beams may generate more uniform lighting conditions while maintaining the spatial filtering advantage described above.

In addition, or as an alternative to, using multiple illumination beams, some embodiments may further increase image resolution by tilting the direction of the objective away from the surface normal. For example, a first image may be captured with the objective tilted off of the surface normal by a first angle. A second image may be captured with the objective tilted off of the surface normal by a second angle. The two images may be combined, forming a composite image. According to various embodiments, the direction of the objective at the first angle, the direction of the objective at the second angle, and at least one illumination beam may be coplanar.

According to various embodiments, the systems and methods described herein for imaging subsurface features may be modified to discern areas of a semiconductor component having different doping properties (e.g., different bandgap energies). For example, the illumination source may be configured to generate illumination having a wavelength with an associated photonic energy that is substantially equal to the bandgap of a doped region of the semiconductor component. As a result, the doped region may attenuate the illumination causing the doped region to appear dark or shaded in the resulting image. Also, in some embodiments, the wavelength of the illumination source may be selected with a photonic energy substantially equal to the bandgap of an un-doped region of the semiconductor component, causing the un-doped region to appear dark or shaded. In various embodiments, the wavelength of the illumination source may be variable. For example, the illumination source may be set to various wavelengths corresponding to the bandgap energies of differently doped regions in the semiconductor component. Each of the differently doped or un-doped regions may appear as a dark or shaded region when the illumination corresponding to each region's bandgap is active.

According to various embodiments, some or all of the embodiments described herein may also be used in conjunction with a polarization techniques. For example, a polarizer may be placed in an optical path between the illumination source and the imaging device. The polarizer may be oriented with a polarization direction parallel to the illumination beam (e.g., perpendicular to the surface of the object). In this way, specular reflection off of the surface of the object may either be minimized (e.g., if the illumination beam is polarized) or its detection may be minimized (e.g., if the polarizer is placed in the path of the imaging device).

FIG. 1 illustrates a cross-sectional view of one embodiment of an object 102 having an outer surface 108 and subsurface features 104, 106 that may be imaged utilizing the side-addressed illumination techniques described herein. The material 110 of the object 102 between the subsurface features 104, 106 and the surface 108 may have an index of refraction at the imaging wavelength range that is greater than that of the surrounding medium 109, which may be air. The techniques and apparatuses described herein may be used to image subsurface features in many contexts. In various embodiments, however, the object 102 may comprise a semiconductor substrate and the features 104, 106 may be components such as transistors, diodes, resistors, metallization lines and/or other components formed from or on the substrate of the object 102. In this case, the imaging wavelength range may comprise some or all of the near infrared range, which is transparent in silicon. The ratio of the indices of refraction of the material 110 over the surrounding medium 109 (e.g. air) may be approximately 3.5.

It will be appreciated that, when the object 102 is a semiconductor device, the material 110 may be any suitable semiconductor material including, for example, silicon, gallium arsenide (GaAs), silicon carbide (SiC), and/or diamond. In some embodiments, the object 102 may be mounted in a flip-chip manner. Accordingly, the features 104, 106 may be visible through the remainder of the object 102 (e.g., the substrate). As viewed through the material 110, the features 104, 106 may be below the surface of the object 102 by any suitable distance d that permits transmission of illumination from an illumination source and reformation of an image by the objective or the objective lens of an imaging device (see FIG. 2). In some embodiments, the distance d may be 700 microns.

Figure 2:
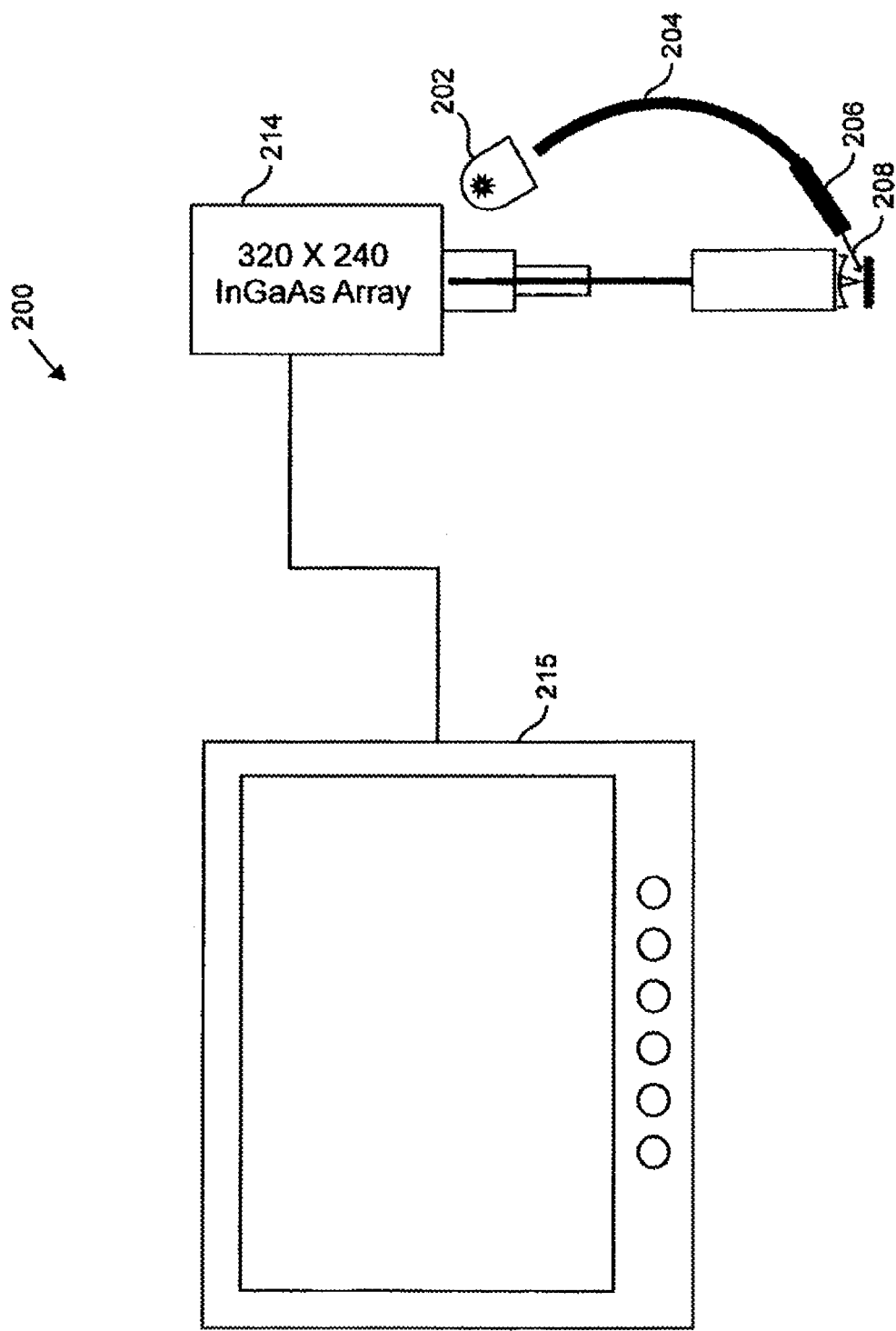
FIG. 2 illustrates one embodiment of a system for side-addressed imaging.

FIG. 2 illustrates one embodiment of a system 200 for side-addressed imaging. The system 200 includes an illumination source 202 optically coupled to a fiber optic bundle 204 (e.g., made of quartz or other suitable material) and a collimating lens 206. According to various embodiments, the source 202 may comprise a tungsten halogen lamp with a gold-plated reflector. It will be appreciated that suitable systems may omit various components such as the fiber optic bundle 204 and collimating lens and/or incorporate some or all of these components into the illumination source 202 itself. Light emitted by the source 202 may be incident on, and may traverse, the fiber optic bundle 204 and collimating lens 206 resulting in a beam 208 incident on the object 102 at an angle offset from the surface normal. Although the source 202 is illustrated as emitting a collimated beam, it will be appreciated that an uncollimated source may be used as well. An objective lens or objective 212 may be positioned approximately along a normal of the object 102 and may direct reflected portions of the beam 208 towards an imaging device 214. The objective 212 may comprise a lens or combination of lenses and/or apertures. The lens or lenses of the objective 212 may comprise a standard lens or, in various embodiments, may comprise a confocal lens for generating three dimensional images. According to various embodiments, the objective 212 may comprise a 1× relay optic and a an NIR 50× long working distance objective, available from MITUTOYO.

The imaging device 214 may comprise any suitable camera or other imaging element capable of sensing the imaging wavelength range. For example, as shown, the imaging device 214 may comprise a 320×240 Indium Gallium Arsenide (InGaAs) array, such as a GOODRICH SU320 sensor with 25 μm pixel pitch. The combination of the MITUTOYO NIR 50× objective 212 and the GOODRICH SU320 sensor may yield a field-of-view of 300 μm×200 μm. It will be appreciated, however, that different sensor sizes and objective components may be used to generate any suitable field of view. The imaging device 214 may capture an image and display it on a monitor 215 or similar visual display device. In addition to, or instead of, displaying the image on the monitor 215, the imaging device 214 may store captured images at a computer readable medium (not shown), such as read only memory (ROM), random access memory (RAM), a hard drive, a flash drive or other data storage device.

According to various embodiments the system 200 may utilize an imaging wavelength or wavelength range that is transparent, or near-transparent, relative to the material 110. For example, when backside imaging is performed through a silicon substrate, the imaging wavelength range may be selected to include wavelengths greater than about 1100 nm. The imaging wavelength range may be implemented in any suitable way. For example, the source 202 may be a broadband source and one or more optical filters may be positioned in the optical path between the source 202 and the imaging device 214. Also, for example, the source 202 may be a narrow-band source that emits only radiation in the imaging wavelength range. In addition to, or instead of these variations, the imaging device 214 may be a narrow band device that is sensitive only to radiation in the imaging wavelength range (e.g., an InGaAs imaging device 214 may be selected with a sensitivity between 900 nm and 1700 nm). In some embodiments, the object 102 may serve as an optical filter. For example, when the object 102 is a silicon substrate and the illumination source 202 is a broadband source, the silicon substrate may tend to absorb all wavelengths other than the near-infrared wavelengths, which are reflected and refracted as described herein.

Figure 3:
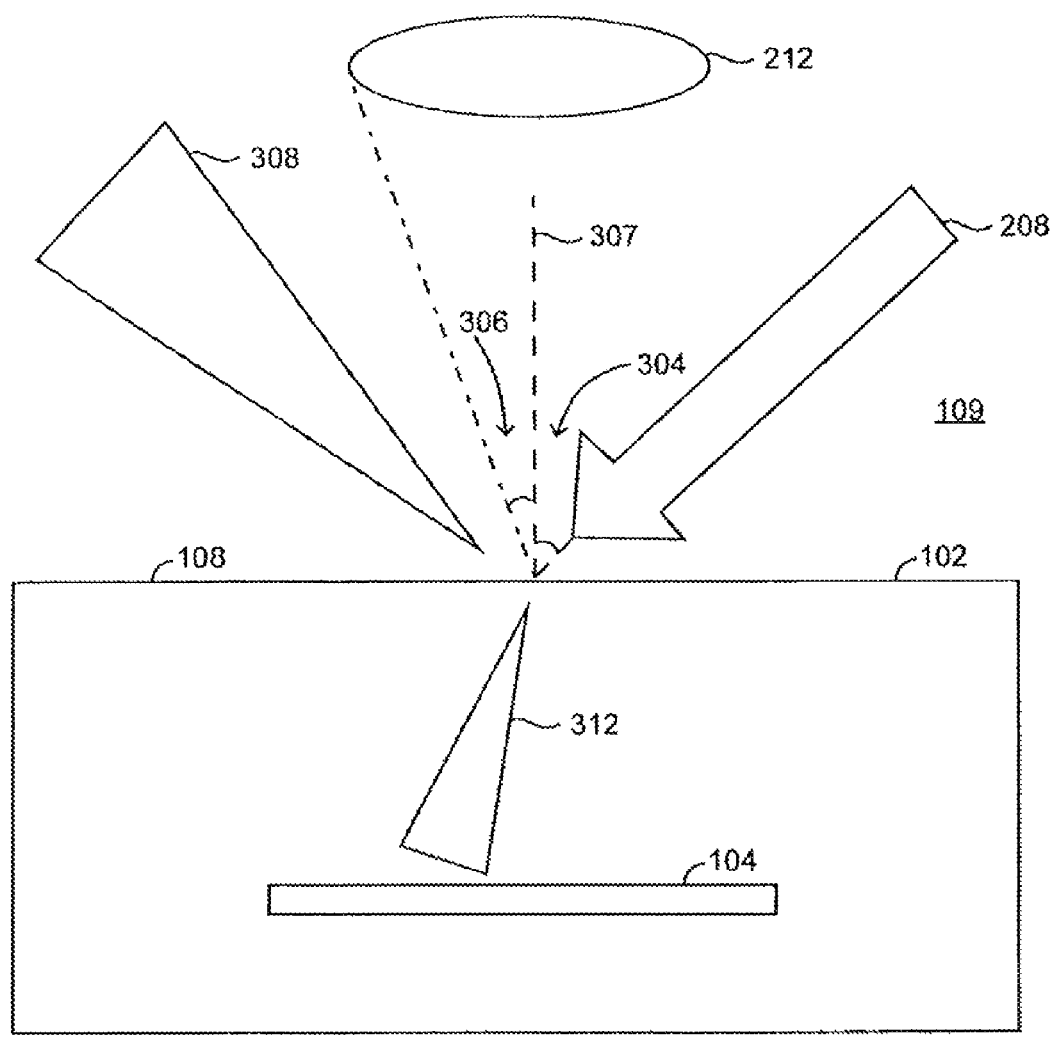
FIG. 3 illustrates one embodiment of the object of FIG. 1 illuminated by an illumination beam.

FIG. 3 illustrates one embodiment of the object 102 showing subsurface feature 104. The incident beam 208 is incident on the object 102 at an angle 304 relative to the surface normal 307. The angle 304 may be set based on the position and orientation of the illumination source 202. The angle 304 may be selected such that specular reflection of the beam 208 off of the object 102 falls outside of an acceptance angle of the objective 212. For example, the angle 304 may be at least equal to the acceptance angle 306 of the objective 212 and less than 90°. It will be appreciated that as the angle 304 increases, the intensity of the light source 202 may also need to be increased to compensate for increasing portions of the illumination beam 208 being reflected off of the object 102 out of the view of the objective 212.

In practice, reflection from the object 102 may not be perfectly specular (e.g., the surface 108 may not be perfectly smooth). Accordingly, the beam 208 may scatter off of the object 102 at a range of angles represented by cone 308. To compensate for this effect, the angle 304 may be selected to be slightly larger than the acceptance angle of the objective 212 such that the actual reflection of the beam 208 off of the object 102 falls substantially outside of the acceptance angle 306 of the objective 212. In this way, the image noise due to surface reflection may be minimized. In one example embodiment where the object 102 is a silicon substrate, the angle 304 may be 45°.

A portion of the beam 208 may be transmitted through the interface between the surrounding medium 109 (e.g., air) and the object 102. Due to the differing indices of refraction between the surrounding medium 109 and the material 110, the resulting light will be refracted towards the normal direction. Also, because the surface 108 of the object 102 may not be perfectly smooth, the refracted portion of the beam 208 may begin to spread, as represented by cone 312. The refracted portion 312 may be incident on and illuminate the feature 104 for imaging.

Figure 4:
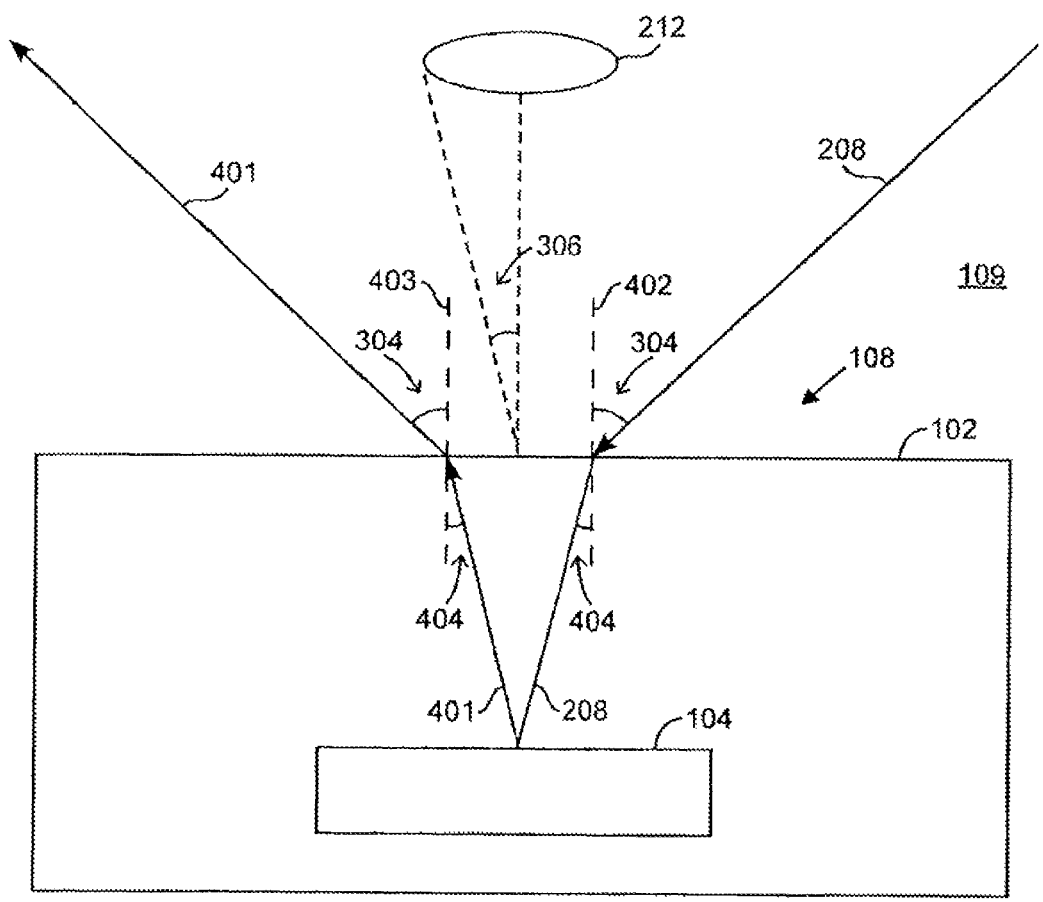
FIG. 4 illustrates one embodiment of the object of FIG. 1 illuminated by the beam oriented at an angle relative to normal of the surface of the object.

FIG. 4 illustrates one embodiment of the object 102 illuminated by the beam 208 oriented at the angle 304 relative to normal of the surface of the object 102 (represented by normal dashed lines 402, 403). At the interface between the object 102 and the surrounding medium 109, the beam 208 may be refracted such that its angle relative to the normal 402 is shown by 404. When the surrounding medium 109 is air (index of refraction ~1), the object 102 is a silicon substrate (index of refraction ~3.5) and the angle 304 is about 45°, given Snell's law, the angle 404 may be about 11.6°. After entering the object 102, the incident beam 208 may reflect off of the feature 104, resulting in a reflected beam 401. The reflected beam 401 may be incident on the surface 108 between the object 102 and the surrounding medium 109 at the angle 404 relative to the normal 403. At the surface 108, the reflected beam 401 may be refracted to the angle 304 relative to the normal 403.

Figure 5:
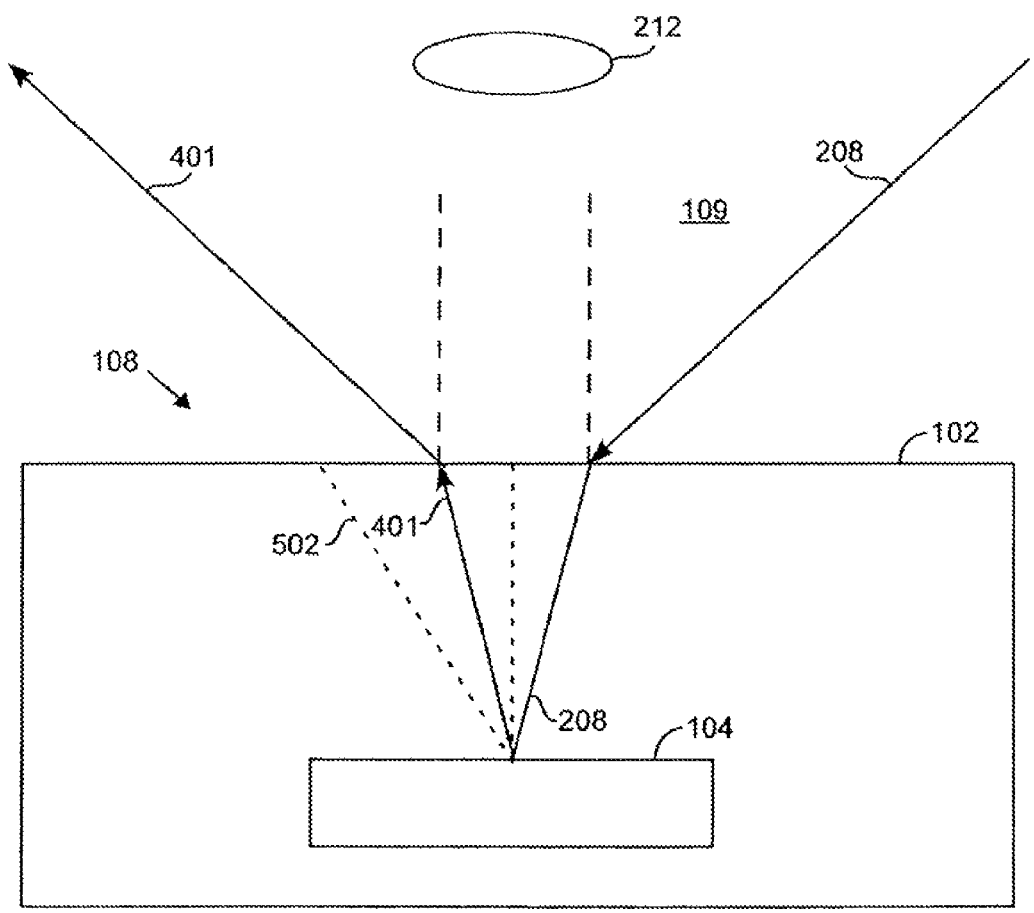
FIG. 5 illustrates one embodiment of the object of FIG. 1 showing a beam reflected off of the surface of a feature of the object over a range of angles.

It can be seen that, as illustrated in FIG. 4, the reflected beam 401 is not incident on the objective 212 within its acceptance angle 306. At least two factors, however, allow portions of the beam 401 to be incident on the objective 212. First, as illustrated in FIG. 3, roughness on the surface 108 of the object 102 may cause the incident beam 208 to actually be incident on the feature 104 over a range of angles, represented by cone 312 shown in FIG. 3. Further, surface roughness of the feature 104 may cause the reflected beam 401 to be scattered over a range 502 of angles, including angles that allow a portion of the reflected beam 401 to be incident on the objective 212 within its acceptance angle (see FIG. 5). It will be appreciated that portions of the beam 401 follow paths similar to those shown in FIG. 4 and, therefore, such portions are not incident on the objective 212. Because a portion of the reflected beam 401 is lost, it may be desirable to choose an illumination source 202 having an intensity relatively greater than what would be used for a similar bright field imaging set-up. For example, in various embodiments, the intensity of the illumination source 202 may be an order of magnitude larger than that used for a similar bright field imaging set-up.

Figure 6:
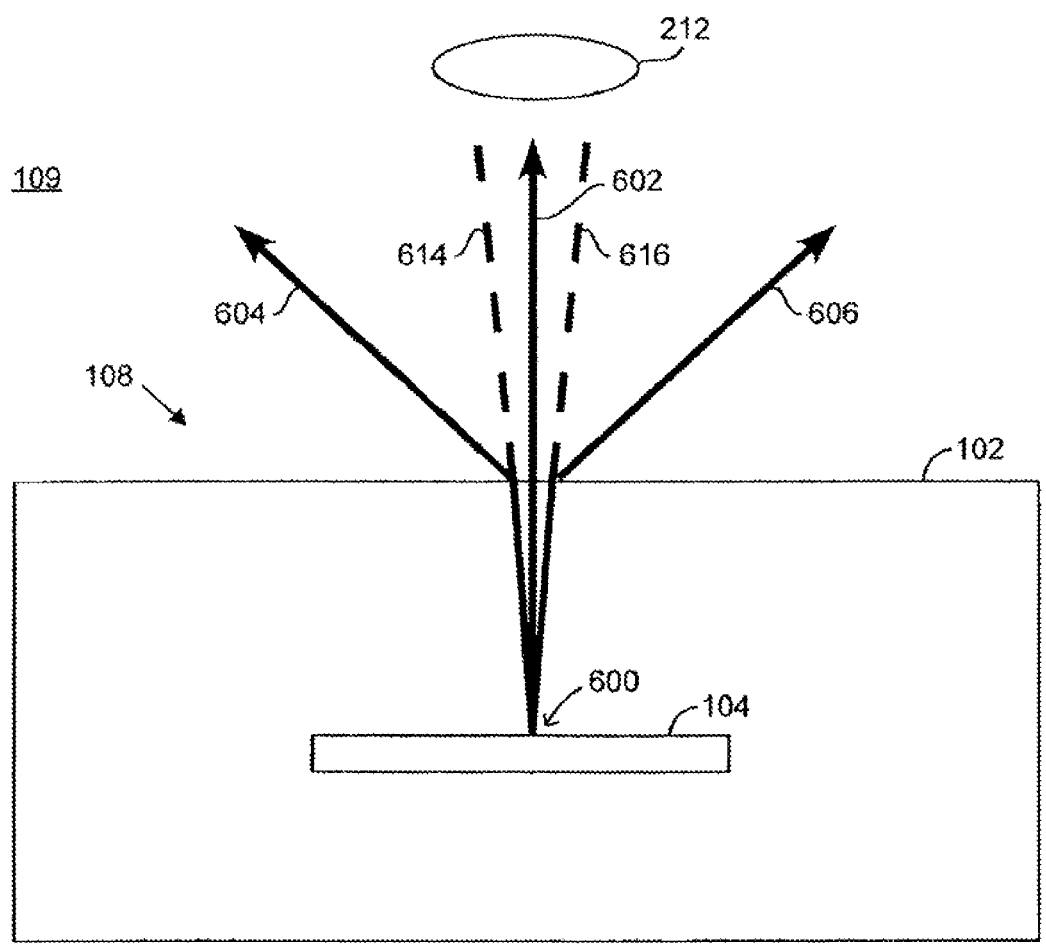
FIG. 6 illustrates one embodiment of the object and feature shown in FIG. 1 showing rays reflected by a point on the feature.

According to various embodiments, refraction at the interface between the surface 108 and the surrounding medium 109 may serve as a spatial filter, increasing the resolution of the image captured by the objective 212 by minimizing the spatial distribution of beams captured from each point of the feature 104. This effect, which can be thought of as an inverse of the Snell's window effect observed under water, is illustrated in FIG. 6. FIG. 6 shows one embodiment of the object 102 and feature 104 including rays 602, 604, 606 reflected by a point 600 on the feature 104. The ray 602 is incident on the surface/surrounding medium 109 interface at an angle within the acceptance range of the objective 212. Accordingly, the ray 602 is received by the objective 212 and transmitted to the imaging device 214 (see FIG. 2). The rays 604 and 606, in contrast, are outside of the acceptance range. As shown by un-refracted paths 614, 616, the rays 604, 606 would ordinarily be incident on objective 212 within its acceptance angle. Because of refraction, however, the rays 604, 606 are bent outside of the acceptance angle of the objective 212. As a result, the minimum spacing between subsurface objects 104 and 106 that can be resolved is based on the wavelength of the incident light 208 divided by the index of refraction of the substrate material 102, thus improving image resolution.

Figure 7:
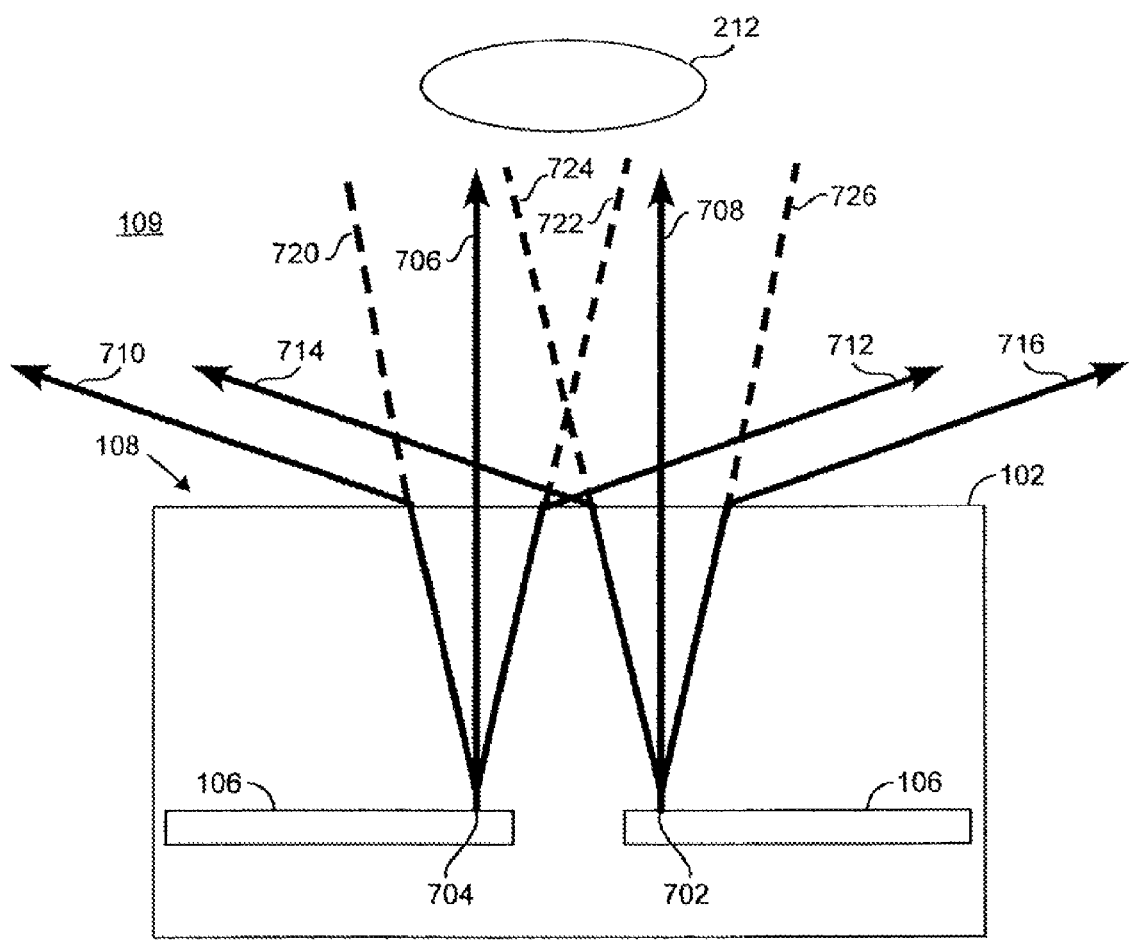

The utility of the spatial filtering effect is demonstrated by FIG. 7, which shows one embodiment of the object 102 showing both of the subsurface features 104, 106. Rays 706, 710 and 712 are reflected off of a point 704 on feature 104. Rays 708, 714 and 716 are reflected off of a point 702 on feature 106. As illustrated, rays 706 and 708 are within the acceptance range and, therefore, are incident on the objective 212. Rays 710, 714, 712 and 716, after refraction at the interface between the object 102 and the surrounding medium 109, are outside of the acceptance range and, therefore, are not incident on the objective 212. Dashed lines 720, 724, 722, 726 indicate the paths of the respective rays 710, 714, 712, 716 absent refraction at the object 102/surrounding medium 109 interface. It will be appreciated that, but for the refraction, ray 714 from point 702 would overlap ray 706 from point 704. This would result in fuzziness and lack of clarity in the resulting image (e.g., in the image, the border between feature 104 and feature 106 would be blurred). As shown, however, the refraction between the object 102 and the surrounding medium 109 minimizes beam overlap from nearby points, thus improving image quality.

Figure 8:
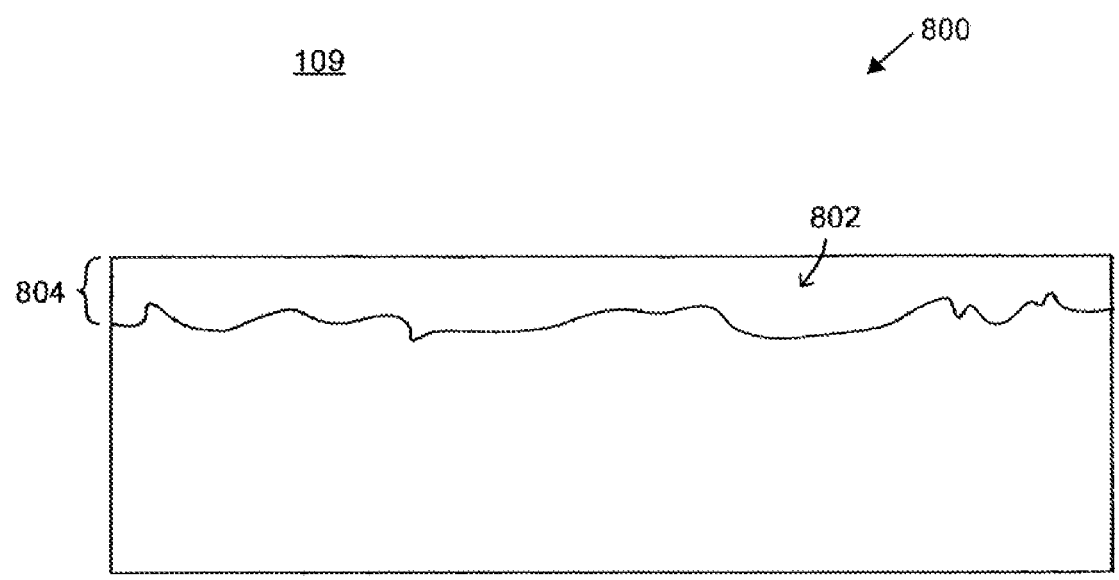
FIG. 8 shows a cross-sectional view of one embodiment of another object having surface features that may be observed utilizing the side addressed illumination techniques described herein.

Also, for example, the apparatuses and methods described herein may be used to image features on the surface of an object by providing a temporary or permanent layer of high refractive index material over the surface prior to imaging. For example, FIG. 8 illustrates a cross-sectional view of one embodiment of another object 800 having surface features 802. The surface features 802 may be imaged by providing a layer 804 of material having a high refractive index at the imaging wavelength range. The layer 804 may be deposited onto the object 800 using any suitable deposition technique. According to various embodiments; the layer 804 may be a fluid, such as an optical coupling fluid, that may be applied to the object 800 in any suitable manner. The layer 804 may be permanent or removable.

Figure 9:
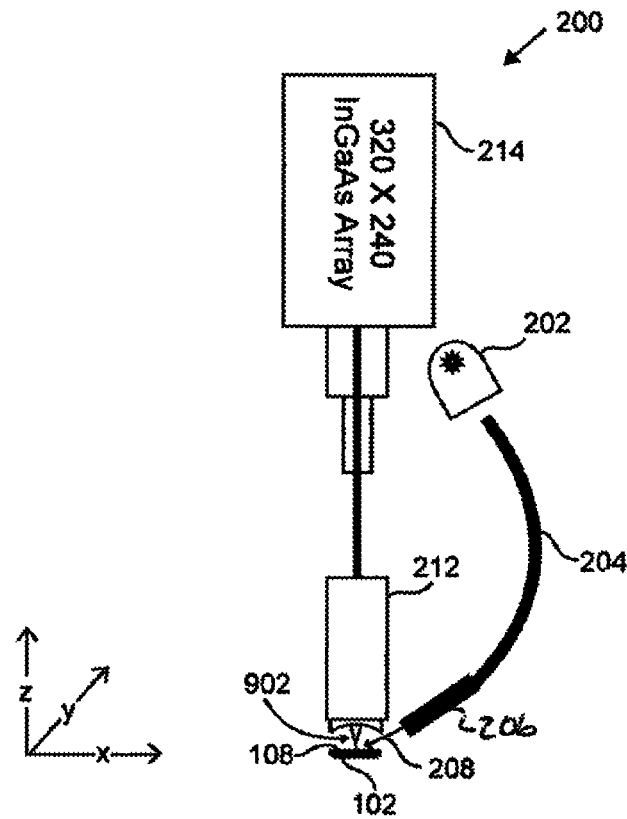
FIG. 9 shows one embodiment of the system of FIG. 2 including the imaging device, the object, the illumination source, and illumination directing elements such as, for example, the fiber optic bundle and collimating lens of FIG. 2.
Figure 10:
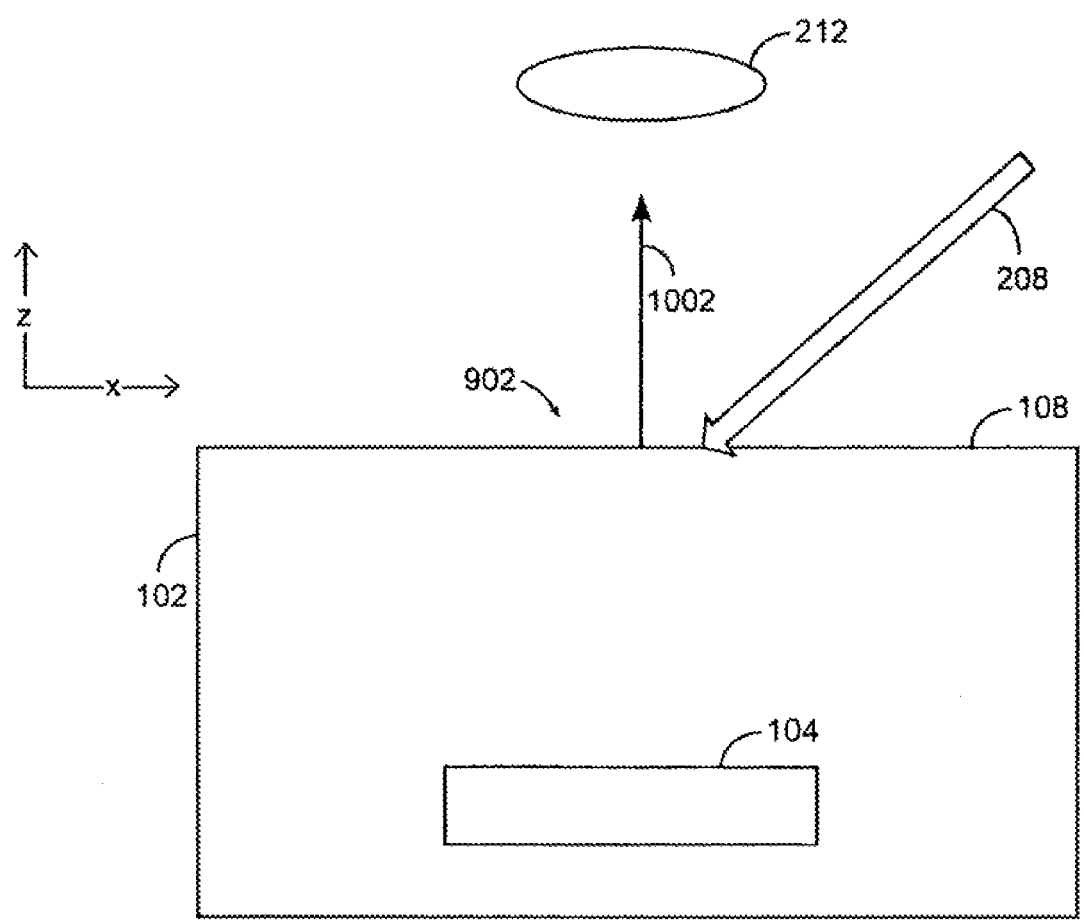
FIG. 10 illustrates a closer view of the object as illustrated in FIG. 9.

FIGS. 9 and 10 illustrate one embodiment of the system 200 configured to provide illumination from multiple angles. For example, FIG. 9 shows one embodiment of the system 200 including the imaging device 214, the illumination source 202, and illumination directing elements such as, for example, the fiber optic bundle 204 and collimating lens 206. Illumination beam 208 is shown incident on an imaging region 902 of the surface 108 of the object 102. Directions in FIG. 9 may be indicated by the x, y and z axes shown. For example, the surface 108 may be in the x-y plane. The z-direction may be normal to the surface 108. FIG. 10 illustrates a closer view of the object 102 as illustrated in FIG. 9. A surface normal 1002 is illustrated normal to the surface 108 in the direction of the z-axis.

Figure 11:
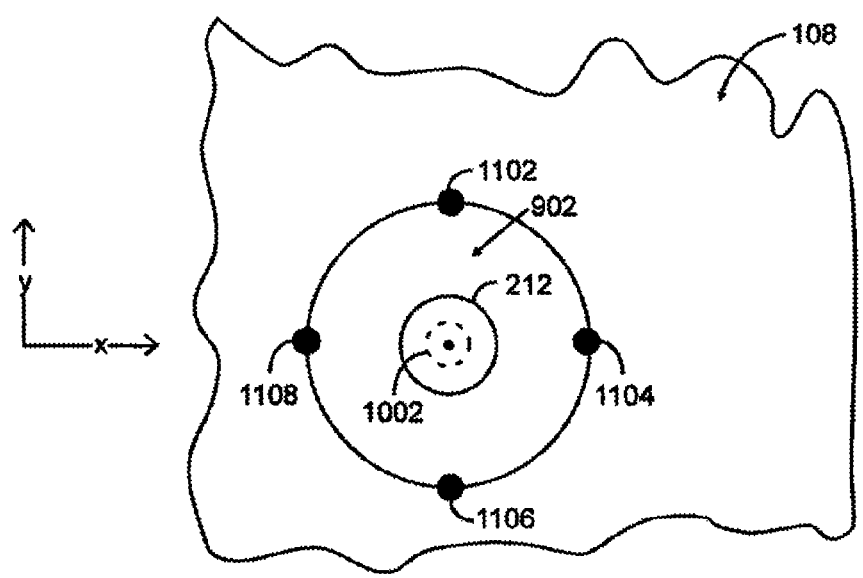
FIG. 11 illustrates a top view of the surface of the object of FIG. 10 showing four different illumination beams.

FIG. 11 illustrates a top view of the surface 108 showing four example illumination beams 1102, 1104, 1106, 1108. Each of the illumination beams 1102, 1104, 1106, 1108 may be directed to the imaging location 902 at an angle relative to the normal 1002. In some embodiments, all of the illumination beams may be positioned at the same angle relative to the normal 1002. In other embodiments, different illumination beams 1102, 1104, 1106, 1108 may have different angles relative to the normal 1002. As illustrated, each of the illumination beams 1102, 1104, 1106, 1108 is rotated about the normal in the x-y plane at various angles relative to one another. For example, the illumination beams 1104 and 1108 may be rotated from the beam 1102 by +90° and −90°, respectively. The beam 1106 may be similarly rotated from the beam 1102 by 180°.

It will be appreciated that the various illumination beams 1102, 1104, 1106, 1108 may be generated by a single illumination source 202, which may be rotated or otherwise directed to the position of each beam 1102, 1104, 1106, 1108. In some embodiments, multiple illumination sources may be used. For example, each beam 1102, 1104, 1106, 1108 may be generated by a separate illumination source. Also, although four illumination beams 1102, 1104, 1106, 1108 are shown, it will be appreciated that beams may be omitted or added. For example, in some embodiments, it may be desirable to have three beams. A first beam may be considered to be positioned at 0°. A second beam may be rotated about the normal 1002 by +45°, and a third beam may be rotated about the normal 1002 by −45°.

According to various embodiments, all of the beams 1102, 1104, 1106 may be illuminated at the same time. In this case, a single image of the imaging region 902 may be captured with all of the illumination beams 1102, 1104, 1106, 1108 active. In some embodiments, however, less than all of the beams 1102, 1104, 1106, 1108 may be illuminated at the same time. For example, in some embodiments, the beams 1102, 1104, 1106, 1108 may be illuminated separately or in a combination of less than all of the beams 1102, 1104, 1106, 1108. A separate image may be captured while each beam or combination of beams 1102, 1104, 1106, 1108 is illuminated. The resulting images may be composted or otherwise combined to form a composite image.

According to various embodiments, the number and orientations of the illumination beam or beams in the x-y plane may be determined based on the orientation of the surface 108 and any sub-surface features 104. For example, illuminating a surface 108 in a direction parallel to and in a direction perpendicular to sub-surface features 104 may, in some embodiments, provide increased resolution. When the object 102 is a semiconductor chip, the sub-surface features 104 may be arranged in a grid-like Manhattan-style configuration. Accordingly, at least two illumination beams may be utilized with the illumination beams aligned with the grid of the sub-surface features 104 and separated from one another about the normal 1002 by 45°. When X-architecture chips or other non-Manhattan-style objects are imaged, different illumination beam directions may be selected to illuminate the parallel and perpendicular directions of major sub-surface features 104.

Figure 12:
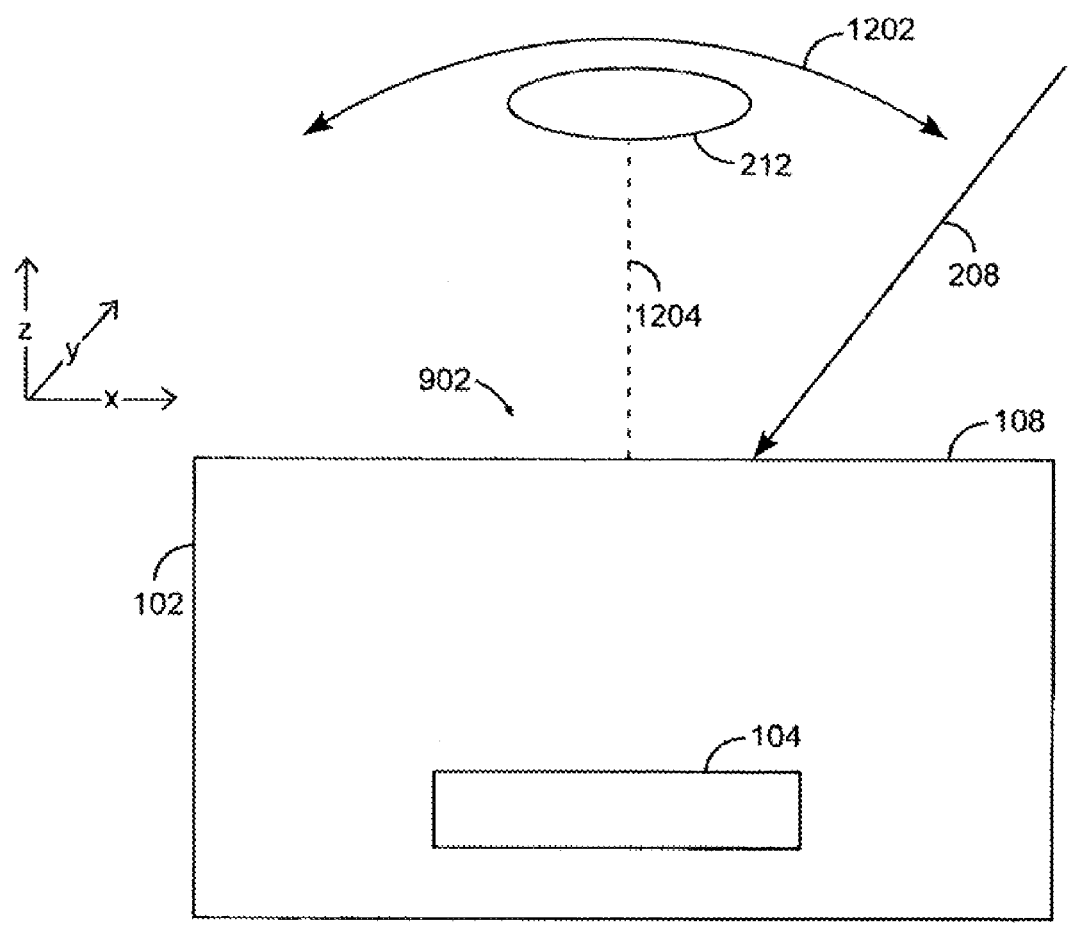
FIG. 12 illustrates one embodiment of the surface and objective illustrating how the objective may be tilted.

In some embodiments, the objective 212 may be tilted relative to the surface normal 1002 to capture images of the imaging region 902 from multiple directions. The captured images may then be composted or otherwise combined to form a composite image. FIG. 12 illustrates one embodiment of the surface 108 and objective 212 showing an arrow 1202 along which the direction 1204 of the objective 212 may be tilted. According to various embodiments, and as indicated by the arrow 1202, the direction 1204 of the objective 212 may be tilted off of the normal 1002 while remaining in the same plane as the illumination beam 208. (Note that in FIG. 12, the normal 1002 and the direction 1204 of the objective 1204 are the same.) In the example shown in FIG. 12, the illumination beam 208 and objective direction 1204 are shown in the x-z plane. Accordingly, in the illustrated example, the direction 1204 objective 212 may be rotated off of the normal 1002 in the x-z plane. It will be appreciated that the illumination beam 208, and therefore the direction of objective 212 tile, need not always be in the x-z plane (e.g., as illustrated in FIG. 11).

Figure 13:
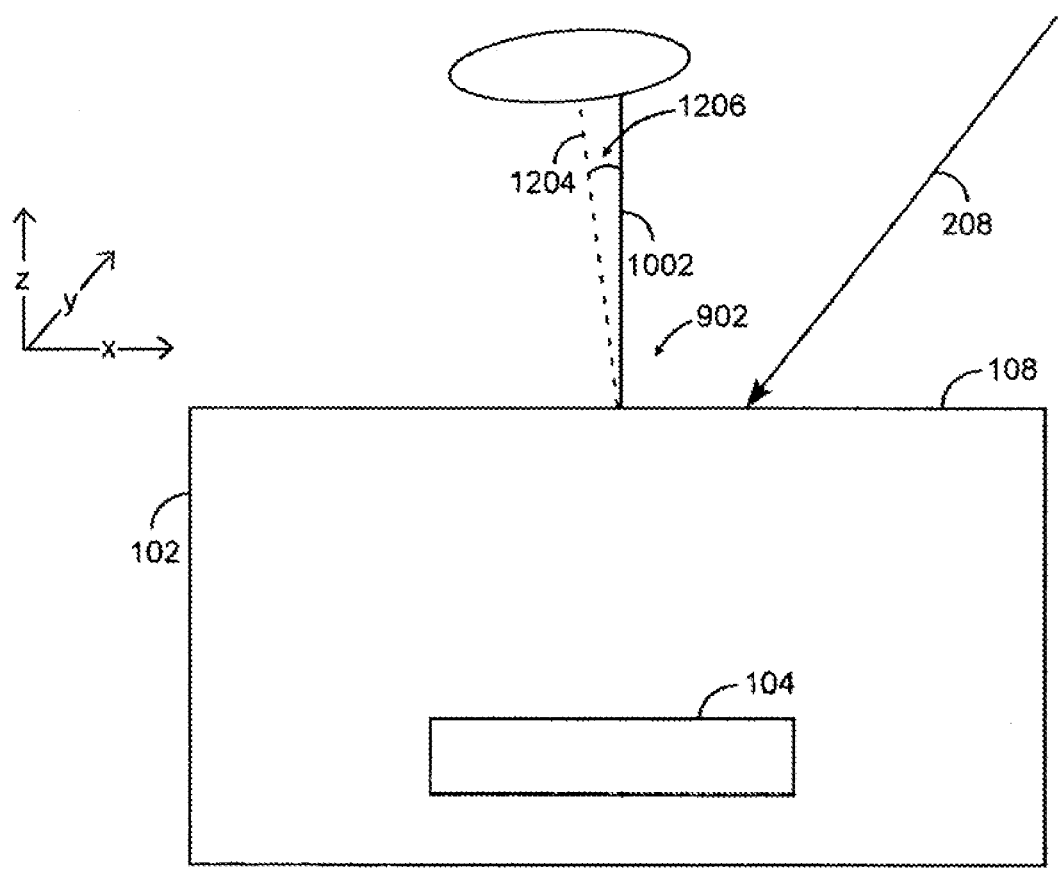
FIG. 13 illustrates one embodiment of the surface and objective with the objective tilted off of the normal by an angle.

The amount of objective 212 tilt may be expressed as an angle between the direction 1204 of the objective 212 and the normal 1002. FIG. 13 illustrates one embodiment of the surface 108 and objective 212 with the objective 212 tilted off of the normal 1002 by an angle 1206. It will be appreciated that the number of images and the objective 212 positions from which the images are captured may vary. For example, according to various embodiments, a first image may be captured with the angle 1206 equal to +10° and a second image may be captured with the angle 1206 equal to −10°.

In some embodiments, multiple illumination beams (as illustrated by FIGS. 9-11) may be utilized in conjunction with multiple objective positions (as illustrated by FIGS. 12-13). For example, when there are multiple illumination beams, a series of images with the objective 212 at different tilt levels, may be captured in each plane containing at least one illumination beam.

In embodiments where multiple images are composted to form a composite image, any suitable image combining algorithms may be used. For example, when two images are combined, stereographic techniques may be used. According to stereographic techniques, a first image from a first angle may be colored with a first hue (e.g. blue) while a second image from a second angle may be colored with a second hue (e.g., green). The two colored images may be superimposed on one another, resulting in a three-dimensional image that may be viewed with appropriate optics (e.g., filters matching the image hues). Stereographic techniques may be useful in situations where two images are complimentary. For example, images taken with the objective 212 tilted by the same amount in two different directions away from the normal 1002 may be complimentary. Also, for example, images taken with illumination beams in the same plane may be complimentary.

Additional image combining techniques may be used, for example, when more than two images are combined. For example, it will be appreciated that composite images may tend to wash out as more component images are combined. Any suitable technique may utilized to minimize this effect. For example, each component image may first be digitally stretched and then overlaid with one another with a given transparency factor (e.g., 50%).

Various embodiments may be directed to systems and methods for imaging objects (e.g., semiconductor objects) in a manner that discerns differences in doping between different regions of the object. For example, when an object is imaged, illumination received by the objective of the imaging device may represent illumination that was reflected or backscattered by subsurface features of the object. It will be appreciated that subsurface features capable of reflecting or backscattering illumination (e.g., reflective subsurface features) may be visible to the imaging device, while subsurface features that are not capable of reflecting or backscattering illumination (e.g., transmissive or non-reflective features) may not be visible to the imaging device. In the context of a semiconductor object, reflective features may include physical features, such as metal lines. It may be desirable, however, to view other non-reflective features of a semiconductor object, such as, for example, implants, wells and other features that represent areas of the object having different doping properties. These features, in various embodiments, may have certain impurities intentionally added so that the features have a doping level different than that of the rest of the semiconductor object. Differences in doping may lead to differences in electrical properties that facilitate the operation of the electrical devices on the semiconductor object. The specific impurities chosen may depend on the desired electrical properties. For example, impurities such as boron or aluminum may create p-type doping, while impurities such as phosphorus, antimony, arsenic, etc., may create n-type doping.

In order to view object areas having different doping properties, illumination may be provided to an object, for example, in the manner described herein above. The wavelength of the illumination, however, may be chosen such that photons of the illumination wavelength are completely or partially absorbed by portions of the object having a first bandgap (or doping) and transmitted by portions of the object having different bandgaps or dopings. This may cause resulting images to show a contrast between differently doped features of the semiconductor object. A semiconductor material generally attenuates or absorbs light having a photonic energy (e.g., the energy of the photons making up the illumination) equal to or greater than its bandgap. As photonic energy increases above the bandgap, the degree of attenuation may generally increase. Similarly, semiconductor materials are generally transparent to illumination having a photonic energy less than the bandgap. Accordingly, the illumination wavelength may be chose so that the illumination energy is substantially equal to or slightly greater than the bandgap of the doped portions of the object, but unequal to or lower than the bandgap of the un-doped portions of the object. In this way, as the illumination passes through doped portions of the semiconductor object, the illumination will be attenuated as photons are absorbed by the doped portions. This attenuation may be visible in images of the object, for example, as dark spots or regions.

The bandgap of a semiconductor describes a difference in energy between charge carriers (e.g., electrons and/or holes) in a conduction band capable of conducting current and substantially immobile charge carriers in a valence band. When a semiconductor object is struck by a photon having a photonic energy substantially equal to the bandgap, the photon may be absorbed by a valence band electron, causing the valence band electron to jump from the valance band to the conduction band. If the semiconductor object is struck by a photon having a photonic energy less than the bandgap of the semiconductor object, then the photon may be transmitted through the semiconductor and not absorbed (e.g., unless the semiconductor object is otherwise opaque at the illumination wavelength). Accordingly, selecting an illumination wavelength having a photonic energy substantially equal to the bandgap of the doped portions of the semiconductor object may cause the doped portions to be visible in resulting images (e.g., as darker sections, as a result of increased attenuation). It will be appreciated that changing the doping of a semiconductor object (e.g., by adding a dopant such as phosphorus, boron, etc.) may change the bandgap of the semiconductor object in the area of the doping.

Figure 14:
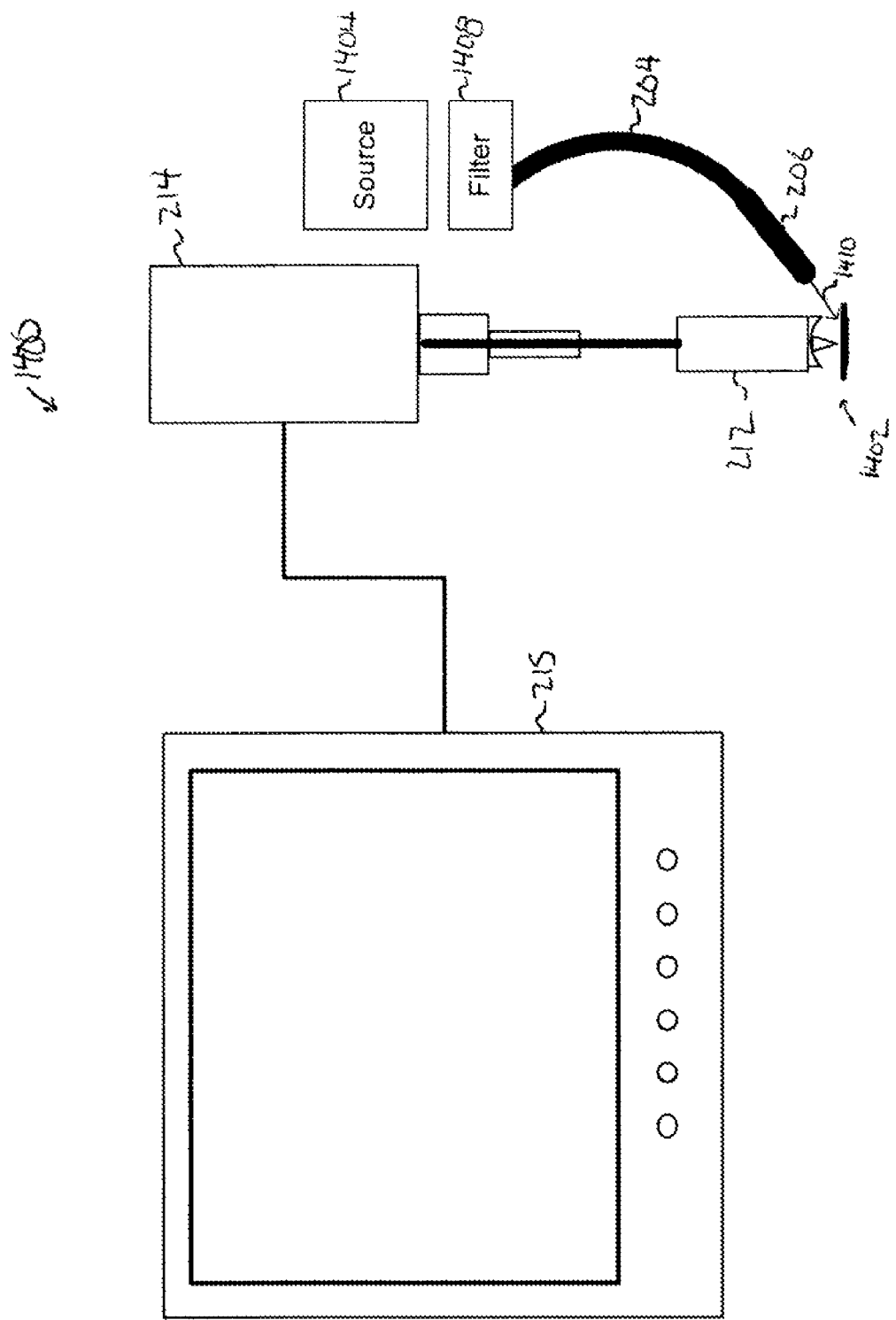
FIG. 14 shows one embodiment of a system for side-addressed imaging that may discern differences in doping in a semiconductor object.

FIG. 14 shows one embodiment of a system 1400 for side-addressed imaging that may discern doped regions in a semiconductor object 1402, such as wells, implants, etc. The system 1400 may comprise an imaging device 214, objective 212 and optional monitor 215, for example, as described herein. An illumination source 1404 may provide an illumination beam 1410 having an illumination wavelength that is substantially transmitted by un-doped portions of the semiconductor object 1402 (e.g., the illumination wavelength may be less than a bandgap of the un-doped portions). The illumination wavelength, however, may have a photonic energy substantially equal to or greater than a bandgap of a doped portion of the semiconductor object 1402. Accordingly, the illumination wavelength may be attenuated by the doped portion. The numerical value of the illumination wavelength may be selected based on the properties of the particular semiconductor and dopants used. For example, intrinsic silicon may have a bandgap of about 1.11 electron Volts (eV), corresponding to about 1117 nm. Silicon with a doping concentration of about 1e20/cm$^3$ may have a bandgap of about 1.01 eV, corresponding to about 1228 nm. Accordingly, for such an object, the illumination wavelength may be selected between about 1117 nm and about 1228 nm. It will be appreciated that the bandgap corresponding to any particular intrinsic or doped material may be found in any suitable theoretical and/or experimental manner. Further, the relationship between bandgap and wavelength may be described in any suitable manner including, for example utilizing the Planck-Einstein equation given by [1]:

$$E = \frac{hc}{\lambda}. \quad [1]$$

In [1], E is energy, λ wavelength, h is Planck's constant, c is the speed of light.

The illumination source 1404 may generate the illumination beam 1410 at the illumination wavelength in any suitable manner. For example, the illumination source 1404 may be a narrow-band source, such as a laser, tuned to a particular illumination wavelength. In some embodiments, the illumination source 1404 may comprise a broadband source, such as a halogen lamp, used in conjunction with an optional optical filter 1408. The optical filter 1408 may be any suitable type of optical filter including, for example, an absorptive filter, a dichroic filter, a diffraction grating, etc. The optical filter 1408 may be a band pass filter having a pass band corresponding to the illumination wavelength (e.g., the wavelength with a photonic energy substantially equal to or greater than the bandgap of a doped portion of the semiconductor object). In various embodiments, the optical filter 1408 may be used in conjunction with narrow band sources having a spectrum that is broader than desired. Also, it will be appreciated that the illumination source 1404 may be used in conjunction with a fiber-optic bundle 204 and collimating lens 206, as described herein. As illustrated in FIG. 14, the optional filter 1408 is positioned between the illumination source 1404 and the fiber bundle 204, although it will be appreciated that the filter 1408 may be positioned at any suitable location in the illumination path.

Figure 15:
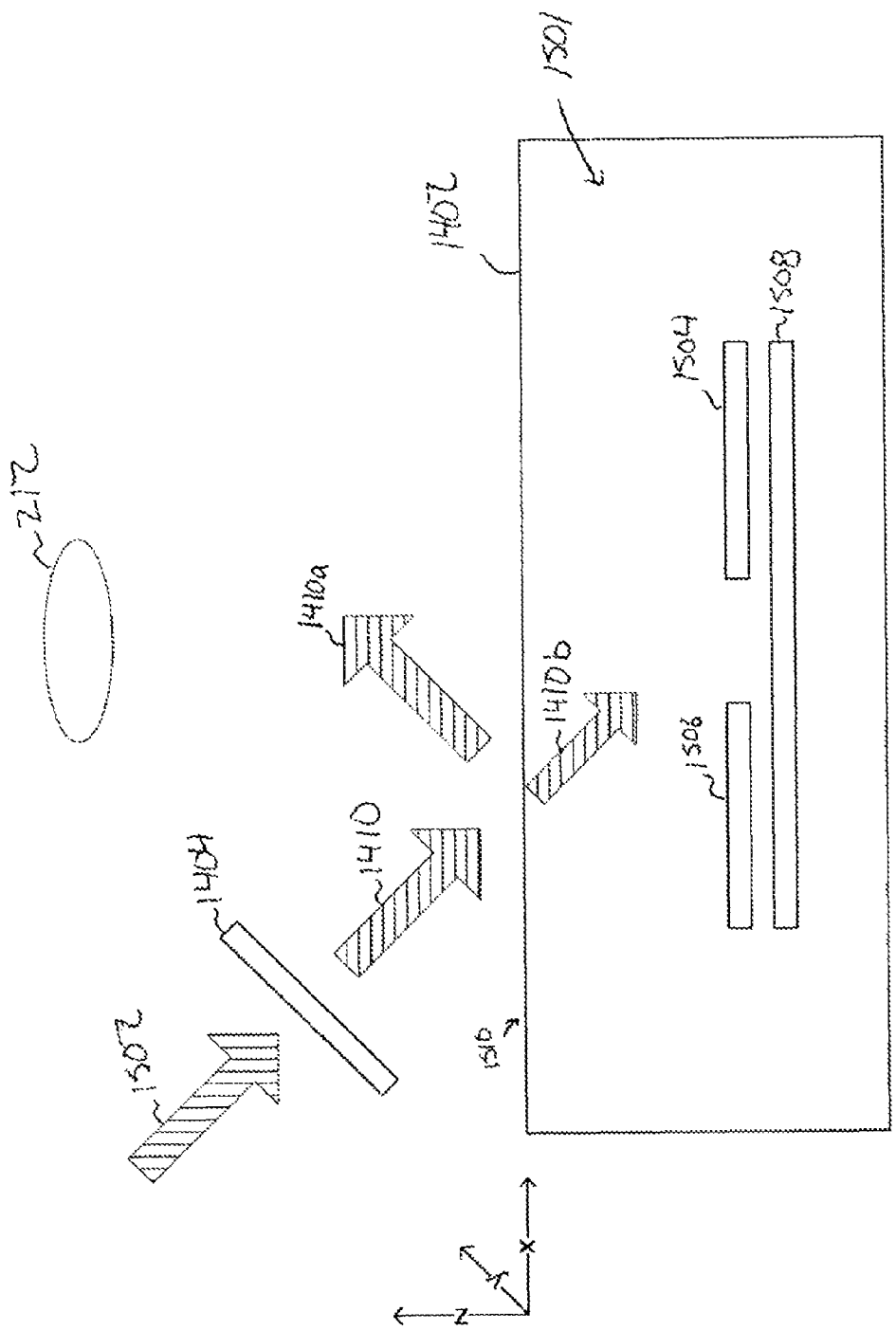
FIG. 15 illustrates one embodiment of the semiconductor object having doped regions and a reflective subsurface feature.

FIG. 15 illustrates one embodiment of the semiconductor object 1402 having doped regions 1504, 1506 and a subsurface feature 1508. Illumination 1502 may be provided by the illumination source 1404. The illumination 1502, for example, may be provided by a broadband source, or a source having a photonic energy spectrum substantially larger than the bandgap of at least one of the doped regions 1504, 1506. Optical filter 1408 may act upon the illumination 1502, producing illumination beam 1410 substantially at the illumination wavelength. (e.g., as described above, a wavelength with a photonic energy spectrum substantially equal to or greater than the bandgap of at least one of the doped regions 1504, 1506). The illumination beam 1410 may impinge upon a surface 1510 of the semiconductor object 1402. According to various embodiments, the illumination beam 1410 may be side-addressed, for example, as described herein with respect to FIGS. 1-8 and 9-13. A portion 1410a of the illumination beam 1410 may be reflected at the surface 1510, while another portion 1410b may be transmitted into the semiconductor object 1402.

The transmitted beam 1410b may be incident upon a reflective subsurface feature 1508, as well as one or more doped regions 1506, 1504. Portions of the beam 1410b may be incident upon one or both of the doped regions 1506, 1504. Illumination incident on the doped regions 1504, 1506 may be attenuated by the doped regions 1504, 1506 (e.g., as photons from the illumination are absorbed by the doped regions 1504, 1506). Subsequently, some illumination incident on the doped regions 1504, 1506 may be incident on the reflective subsurface feature 1508 and reflected back towards the surface 1510. At this point, the illumination may again pass through the doped regions 1504, 1506, and back to the surface 1510. Some of this illumination will reach the objective 212 and form part of a captured image to be stored, and/or viewed on optional monitor 215.

Figure 16:
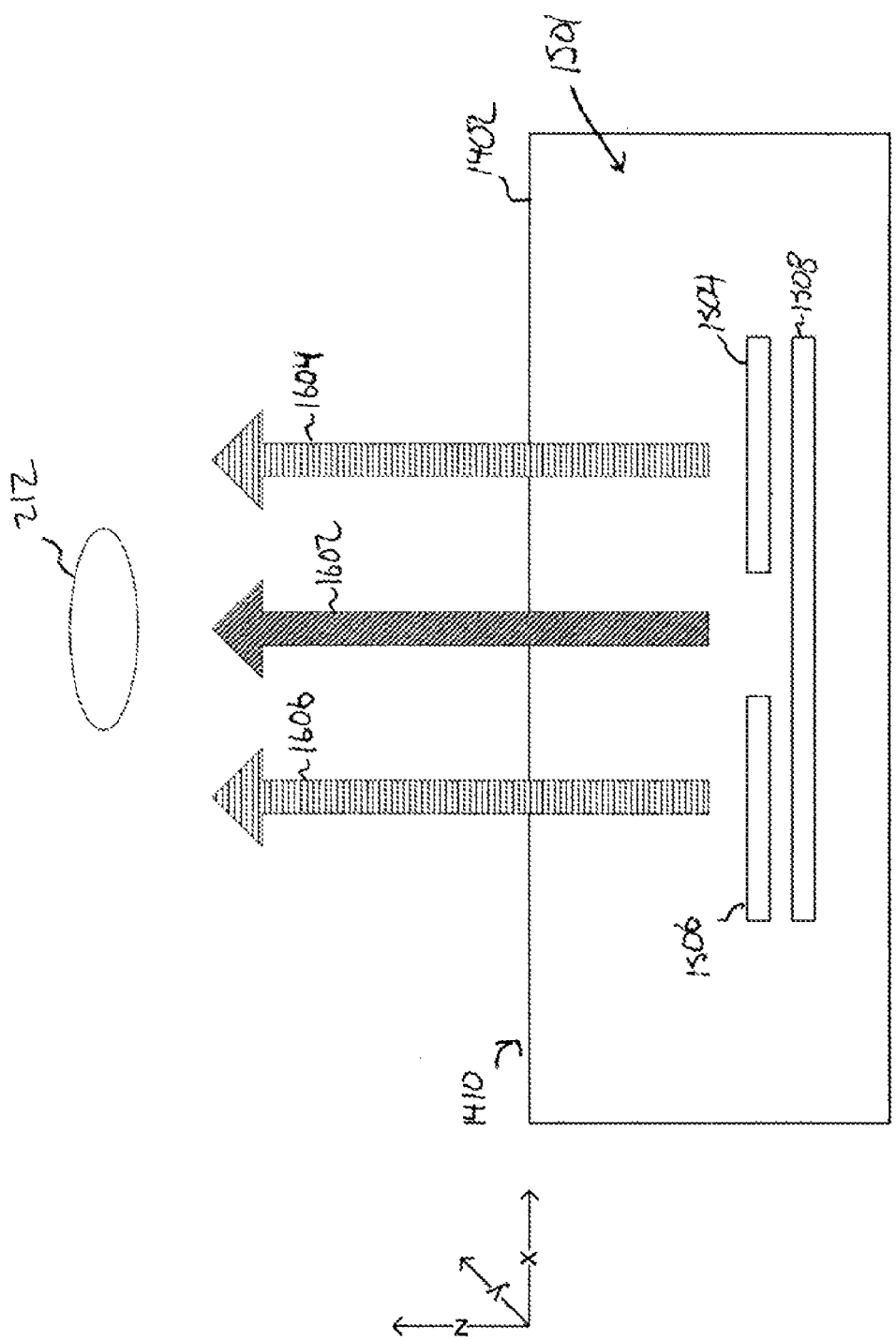
FIG. 16 illustrates one embodiment of the semiconductor object having doped regions, and a reflective subsurface feature showing illumination reflected towards the objective.

FIG. 16 illustrates one embodiment of the semiconductor object 1402 having doped regions, 1504, 1506 and a reflective subsurface feature 1508 showing illumination reflected towards the objective 212. Illumination 1602 may have been incident on the reflective feature 1508, while illumination 1604, 1606 may have been incident on the reflective feature 1508 and passed through the doped regions 1504, 1506. Accordingly, illumination 1604, 1606 may be attenuated relative to illumination 1602. For this reason, portions of the semiconductor object 1402 corresponding to the doped regions 1504, 1506 may appear in an image (e.g., formed at the imaging device 214 via the objective lens 212) as dark or attenuated spots.

According to various embodiments, the illumination wavelength may be selected to have a photonic energy lower than a bandgap of the un-doped portion 1501 of the semiconductor object 1402. The illumination wavelength may also have a photonic energy greater than or equal to a bandgap of the doped portions 1504, 1506. Accordingly, the illumination will be transmitted or passed by the un-doped portion 1501 and attenuated by the doped portions 1504, 1506. As a result, the doped portions 1504, 1506 may appear in the resulting image as darker regions. Selecting the illumination wavelength with a photonic energy substantially equal to or lower than the bandgap of the un-doped portion 1501 of the semiconductor object 1402 may be desirable, for example, in embodiments where the thickness of the doped regions 1504, 1506 is large relative to the depth of the reflective subsurface feature 1508.

Using a single illumination wavelength may allow the visualization of doped regions having a bandgap about equal to or greater than the photonic energy of the selected illumination wavelength. Not all doped regions, however, have the same bandgap. For example, the bandgap of any given doped region may depend the degree of doping, the type of doping (e.g., p-type, n-type), etc. Accordingly, various embodiments may utilize multiple illumination wavelengths in order to image doped regions having different bandgap energies.

Figure 17:
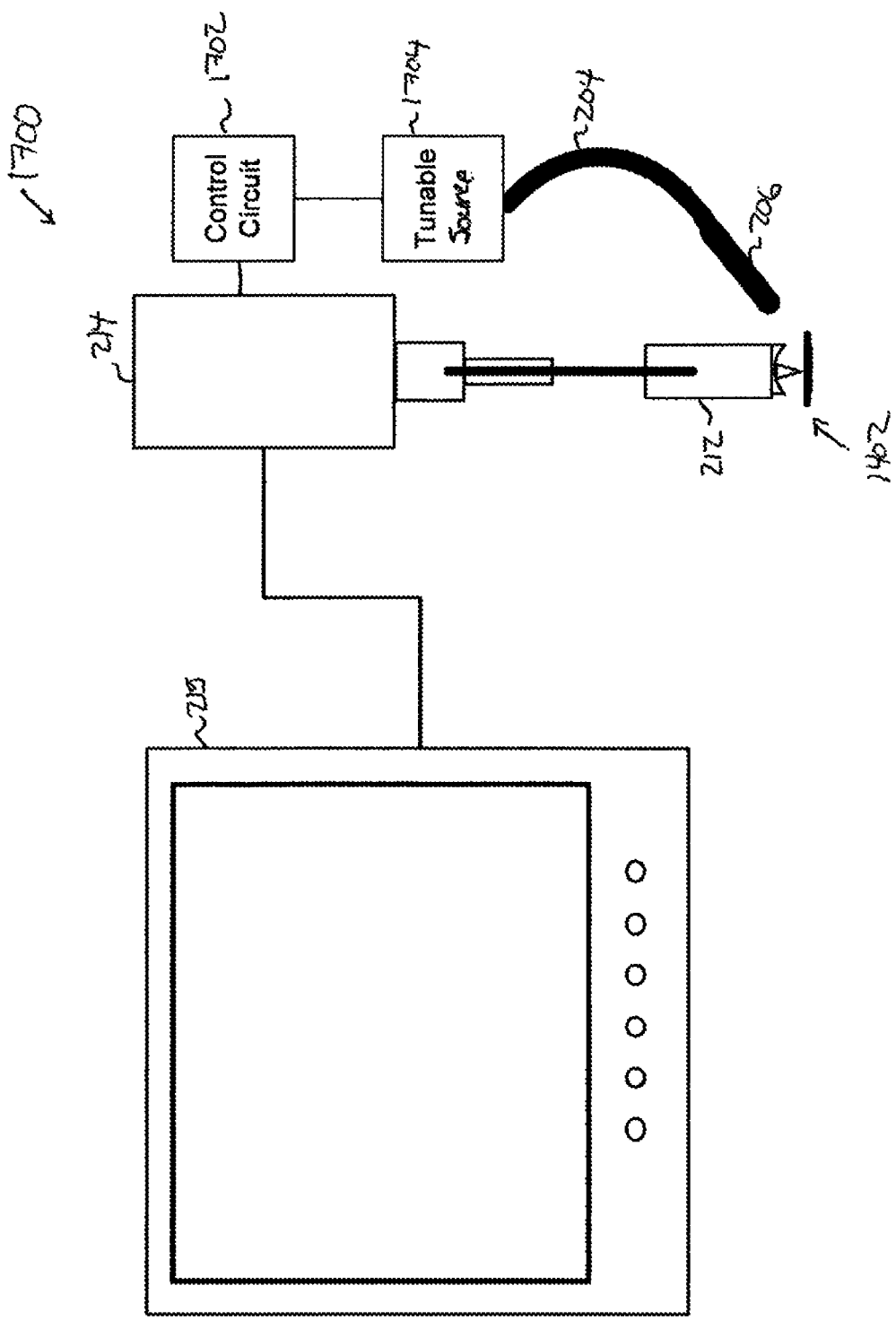
FIG. 17 illustrates one embodiment of a system for side-addressed imaging that may discern differences in doping in a semiconductor object utilizing multiple illumination wavelengths.

FIG. 17 illustrates one embodiment of a system 1700 for side-addressed imaging that may discern differences in doping concentration in a semiconductor object 1402 utilizing multiple illumination wavelengths. In place of, or in addition to, the illumination sources 202, 1404 described herein, the system 1700 may comprise a tunable illumination source 1704 capable of alternately, or simultaneously, providing illumination over a continuous or discrete range of illumination wavelengths. The tunable illumination source 1704 may be, for example, a tunable laser, an array of narrow band lasers, a broadband source in conjunction with a tunable filter, etc. For example, a tunable filter may comprise a filter wheel or other suitable mechanical device including multiple optical band pass filters that may be alternately or simultaneously placed into and/or removed from the optical path of the source.

A control circuit 1702 may control the tunable illumination source 1704. In some embodiments, the control circuit 1702 may also control the imaging device 214 (e.g., to initiate an image capture). The control circuit 1702 may be any suitable type of analog and/or digital device. For example, in various embodiments, the control circuit 1702 may be and/or comprise a microcontroller, a microprocessor, a programmable logic controller (PLC), etc. In various embodiments, the control circuit 1702 may be configured to vary and/or sweep the illumination wavelength over a range. The range may be selected, for example, to include wavelengths having photonic energies about equivalent to or less than bandgap energies of the un-doped semiconductor device 1402, as well as about equivalent to or greater than the bandgap energies of an expected range of doped regions. The range may be continuous or discrete.

Figure 18:
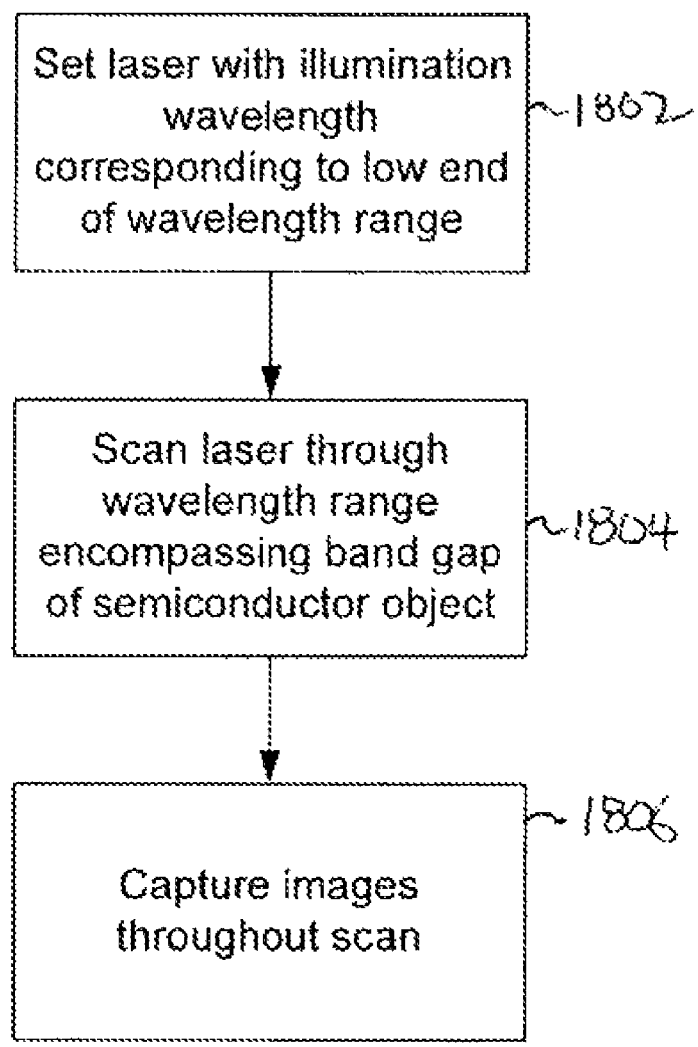
FIG. 18 illustrates one embodiment of a process that may be executed by the control circuit of FIG. 17 to image a semiconductor device including doped and un-doped regions having a range of bandgap energies.

FIG. 18 illustrates one embodiment of a process 1800 that may be executed by the control circuit 1702 to image the semiconductor device 1402, including doped and un-doped regions having a range of bandgap energies. At 1802, the control circuit 1702 may set the laser 1704 at an illumination wavelength at the low end of a scanning illumination wavelength range. The scanning illumination wavelength range may comprise wavelengths having photonic energies spanning a range of bandgap energies expected to be encountered in the doped and un-doped regions of the semiconductor device 1402. At 1804, the control circuit 1702 may scan the laser 1704 through the illumination wavelength range. The scan may be continuous and/or discrete, for example, based on the nature of the control circuit 1702 and the laser or other variable wavelength source. During the scan (1806), the control circuit 1702 may periodically capture images of the semiconductor device 1402. For example, images may be captured periodically in time (e.g., every X milliseconds) or periodically by wavelength (e.g., every X nanometers).

The images resulting from 1806 may show the semiconductor device 1402, including different regions having different dopings and, therefore, different bandgap energies. For example, as the illumination wavelength reaches a wavelength having a photonic energy corresponding to or slightly greater than the bandgap of a first doped region, the first doped region may be visible in corresponding image (e.g., as dark spots or regions because of attenuation due to photonic absorption). Likewise, as the illumination wavelength reaches a wavelength having a photonic energy corresponding to or slightly greater than the bandgap of a second doped region, the second doped region may be visible in the corresponding image. As the illumination wavelength reaches wavelengths having photonic energies greater than the bandgap of the different doped regions, the regions may absorb more of the illumination and, thereby, appear darker. Although the process flow 1800 describes beginning a scan through the illumination wavelength range at a low end of the range and scanning up, it will be appreciated that any suitable scanning pattern may be used. For example, the control circuit 1702 may begin at a high end of the range and scan down or may skip between different portions of the range. Also, it will be appreciated that the illumination wavelength range may, but need not be continuous. For example, the illumination wavelength may include a set of discrete wavelengths having photonic energies clustered based on the bandgap energies expected to be encountered in the semiconductor device 1402.

Figure 19:
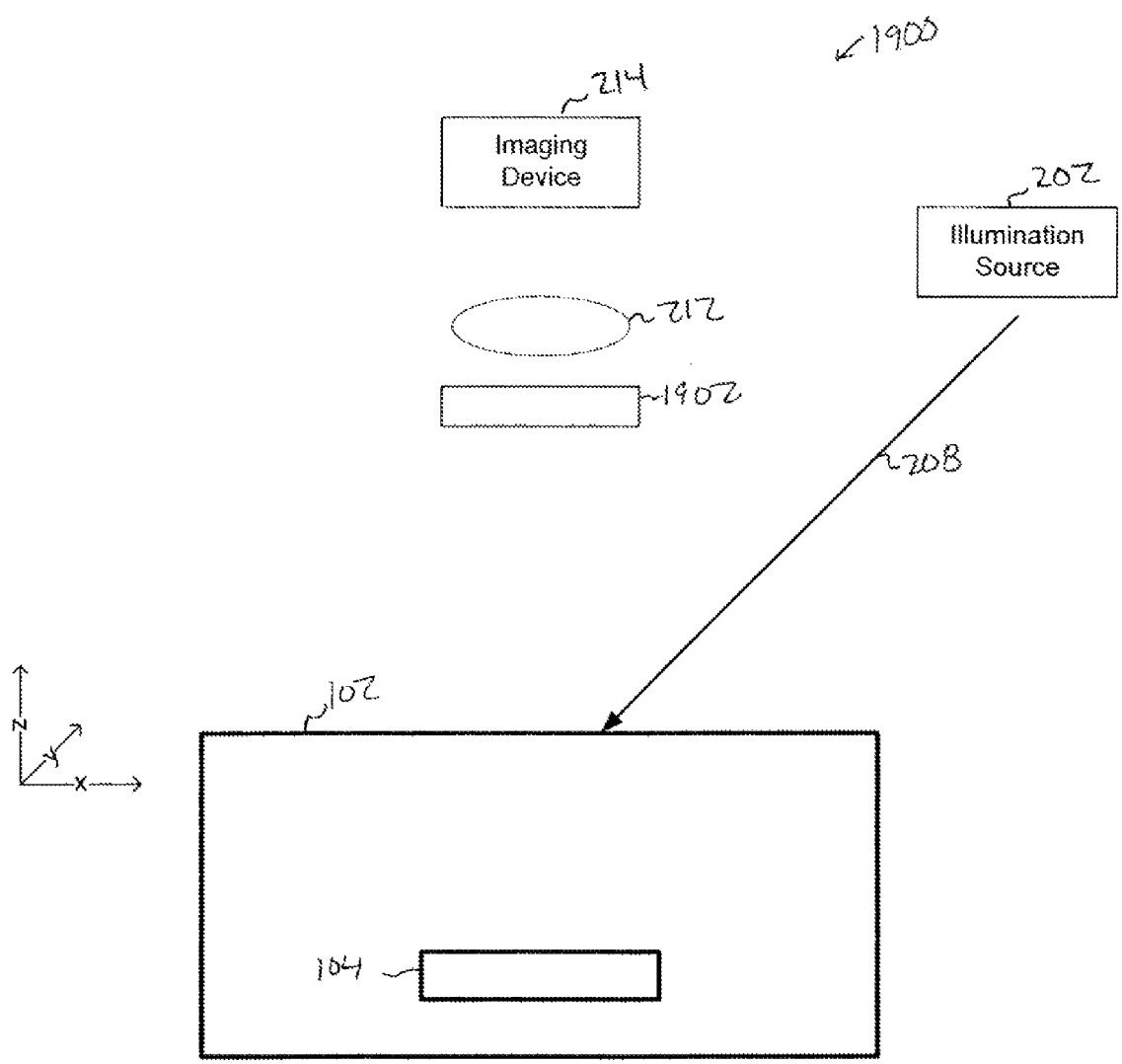
FIG. 19 illustrates one embodiment of the object of FIG. 1 showing a polarizer positioned in the path of the imaging device.

According to various embodiments, undesired specular scatter and/or reflection from the surface of the object 102 (and/or from surface features 102) may be minimized utilizing polarization. For example, FIG. 19 illustrates one embodiment of the object 102 showing a polarizer 1902 positioned in the path of the imaging device 214. The polarizer may have a polarization direction parallel to the illumination beam 208. For example, the polarization direction may be parallel to the illumination beam 208 in a plane that is parallel to the surface of the object 108. For example, any portion of the illumination beam 208 that is reflected by the surface of the object 102 and still is incident on the imaging device 214 may have a significant portion that, due to specular reflection at the surface of the object 102, is polarized perpendicular to the direction of the illumination beam 208. Placing the polarizer 1902, with the cross-polarization direction (e.g., parallel to the direction of the illumination beam) may attenuate this undesirable reflected illumination, further improving the sharpness and/or acuity if the resulting image. It will be appreciated that any suitable means for generating polarized illumination may be used. Also, for example, when a polarizer 1902 is used, as shown, it may be placed at any point in the optical path between the illumination source 202 and the imaging device 214. For example, the polarizer may be placed between the object 102 and the objective 212 as shown. Also, in some embodiments, the polarizer 1902 may be place between the objective 212 and the imaging device 214. Also, in some embodiments, the polarizer 1902 may be placed in the path of the illumination beam 208 before it is incident on the object. In some embodiments, polarizers may be included in both the incident and collected paths.

Although the figures above are described in the context of backside imaging of semiconductor devices, it will be appreciated that the apparatuses and methods disclosed herein may be used in various other contexts as well. For example, the apparatuses and methods used herein may be used to image any subsurface features where the index of refraction of material between a surface of an object and subsurface features of the object is relatively geater than that of the surrounding medium 109.

It is to be understood that the figures and descriptions of the present invention have been simplified to illustrate elements that are relevant for a clear understanding of the present invention, while eliminating other elements, for purposes of clarity. Those of ordinary skill in the art will recognize that these and other elements may be desirable. However, because such elements are well known in the art and because they do not facilitate a better understanding of the present invention, a discussion of such elements is not provided herein.

In various embodiments disclosed herein, a single component may be replaced by multiple components and multiple components may be replaced by a single component to perform a given function or functions. Except where such substitution would not be operative, such substitution is within the intended scope of the embodiments.

While various embodiments have been described herein, it should be apparent that various modifications, alterations, and adaptations to those embodiments may occur to persons skilled in the art with attainment of at least some of the advantages. The disclosed embodiments are therefore intended to include all such modifications, alterations, and adaptations without departing from the scope of the embodiments as set forth herein.

We claim:

1. A system for imaging subsurface features of a semiconductor object comprising a first region having a first doping property and a second region having a second doping property, the semiconductor object comprising subsurface features and material between a surface of the semiconductor object and the subsurface features, the material having an index of refraction that is greater than an index of refraction of a surrounding medium in contact with the surface of the semiconductor object, the system comprising:

an imaging device comprising an objective, wherein the imaging device is sensitive to a first wavelength;

an illumination source to emit illumination substantially at the first wavelength, wherein the illumination is directed towards the surface of the semiconductor object at a first angle relative to a normal of the surface, wherein the first angle is greater than an acceptance angle of the objective of the imaging device, and wherein the first wavelength has a photonic energy greater than a bandgap of the first region and less than a bandgap of the second region.

2. The system of claim 1, wherein the first region is intrinsic silicon and the second region is doped silicon.

3. The system of claim 2, wherein:
the bandgap of the first region is about 1.11eV;
the band gap of the second region is about 1.01eV; and
the first wavelength is between 1117 nm and 1228 nm.

4. The system of claim 1, wherein the illumination source comprises an optical band pass filter for filtering illumination not substantially at the first wavelength.

5. The system of claim 4, wherein the optical band pass filter is selected from the group consisting of an absorptive filter, a diffraction grating, and a dichroic filter.

6. The system of claim 1, wherein the illumination source comprises a narrow band source at about the first wavelength.

7. The system of claim 1, wherein the first region is doped and the second region is substantially undoped.

8. The system of claim 1, wherein the first region is at least one of a p-type region and an n-type region.

9. The system of claim 1, wherein the first region is substantially undoped and the second region is doped.

10. The system of claim 1, wherein the first region and the second region are doped.

11. The system of claim 1, wherein the illumination source is a tunable illumination source, and further comprising a control circuit for controlling the illumination source.

12. The system of claim 11, wherein the control circuit is programmed to:

tune the illumination source to the first wavelength;
cause the imaging device to capture a first image;
tune the illumination source to a second wavelength, wherein the second wavelength has a photonic energy substantially equal to a bandgap of the second region; and
cause the imaging device to capture a second image.

13. The system of claim 11, wherein the control circuit is programmed to:

sweep the illumination emitted by the illumination source across a wavelength range comprising the first wavelength and a second wavelength having a photonic energy substantially equal to a bandgap of the second region; and
cause the imaging device to periodically capture images during the sweep.

14. The system of claim 13, wherein the periodically capturing of images during the sweep comprises at least one of periodically capturing images by time and periodically capturing images by wavelength.

15. The system of claim 1, further comprising a polarizer positioned in an optical path between the illumination source and the imaging device, wherein the polarizer has a polarization direction substantially parallel to a direction of the illumination emitted by the illumination source.

16. A method for imaging subsurface features of a semiconductor object comprising a first region having a first doping property and a second region having a second doping property, the semiconductor object comprising subsurface features and material between a surface of the semiconductor object and the subsurface features, the material having an index of refraction that is greater than an index of refraction of a surrounding medium in contact with the surface of the semiconductor object, the method comprising:

emitting, by an illumination source, illumination substantially at a first wavelength, wherein the illumination directed towards the surface of the semiconductor object at a first angle relative to a normal of the surface, wherein the first angle is greater than an acceptance angle of the objective of the imaging device, and wherein the first wavelength has a photonic energy greater than a bandgap of the first region and less than a bandgap of the second region; and capturing, by an imaging device, an image of the semiconductor object under the illumination.

17. The method of claim 16, wherein the first region is intrinsic silicon and the second region is doped silicon.

18. The method of claim 17, wherein:
the bandgap of the first region is about 1.11eV;
the band gap of the second region is about 1.01eV; and
the first wavelength is between 1117 nm and 1228 nm.

19. The method of claim 16, wherein the illumination source comprises an optical band pass filter for filtering illumination not substantially at the first wavelength.

20. The method of claim 19, wherein the optical band pass filter is selected from the group consisting of an absorptive filter, a diffraction grating, and a dichroic filter.

21. The method of claim 16, wherein the illumination source comprises a narrow band source at about the first wavelength.

22. The method of claim 16, wherein the first region is doped and the second region is substantially undoped.

23. The method of claim 16, wherein the first region is at least one of a p-type region and an n-type region.

24. The method of claim 16, wherein the first region is substantially undoped and the second region is doped.

25. The method of claim 16, wherein the first region and the second region are doped.

26. The method of claim 16, wherein the illumination source is a tunable illumination source.

27. The method of claim 26, further comprising:
tuning the illumination source to the first wavelength;
capturing the image of the semiconductor object under the illumination;
tuning the illumination source to a second wavelength, wherein the second wavelength has a photonic energy substantially equal to a bandgap of the second region; and
capturing a second image of the semiconductor object under the illumination.

28. The method of claim 26, further comprising:
sweeping the illumination emitted by the illumination source across a wavelength range comprising the first wavelength and a second wavelength having a photonic energy substantially equal to a bandgap of the second region; and
during the sweep, periodically capturing images of the semiconductor object.

29. The method of claim 28, wherein the periodically capturing images during the sweep comprises at least one of periodically capturing images by time and periodically capturing images by wavelength.

30. The method of claim 16, further comprising polarizing the illumination in a direction substantially parallel to a direction of the illumination.

* * * * *